(12) United States Patent
Chatterjee et al.

(10) Patent No.: US 9,682,926 B2
(45) Date of Patent: Jun. 20, 2017

(54) CANCER CHEMOTHERAPEUTIC AGENT/FORMULATION, MANUFACTURE AND USE THEREOF

(71) Applicants: Bose Institute, Kolkata (IN); West Bengal State University, Kolkata (IN)

(72) Inventors: Subhrangsu Chatterjee, Kolkata (IN); Anirban Bhunia, Kolkata (IN); Deba Prasad Mandal, Kolkata (IN); Shamee Bhattacharjee, Kolkata (IN)

(73) Assignees: Bose Institute, Kolkata (IN); West Bengal State University, Kolkata (IN)

( * ) Notice: Subject to any disclaimer, the term of this patent is extended or adjusted under 35 U.S.C. 154(b) by 0 days.

(21) Appl. No.: 14/428,836

(22) PCT Filed: Sep. 27, 2013

(86) PCT No.: PCT/IN2013/000593
§ 371 (c)(1),
(2) Date: Mar. 17, 2015

(87) PCT Pub. No.: WO2014/049619
PCT Pub. Date: Apr. 3, 2014

(65) Prior Publication Data
US 2016/0023996 A1   Jan. 28, 2016

(30) Foreign Application Priority Data

Sep. 28, 2012  (IN) .......................... 1120/KOL/2012

(51) Int. Cl.
| | | |
|---|---|---|
| C07C 255/24 | (2006.01) | |
| C07C 251/24 | (2006.01) | |
| A61K 31/275 | (2006.01) | |
| C07C 253/30 | (2006.01) | |
| A61K 9/00 | (2006.01) | |

(52) U.S. Cl.
CPC .......... *C07C 255/24* (2013.01); *A61K 9/0019* (2013.01); *A61K 31/275* (2013.01); *C07C 253/30* (2013.01); *C07C 251/24* (2013.01)

(58) Field of Classification Search
CPC ........................... C07C 255/24; C07C 251/24
See application file for complete search history.

(56) References Cited

PUBLICATIONS

Savjani et al. International Scholarly Research Network, Jul. 2012, vol. 2012, pp. 1-10.*
Golan et al. (Principles of Pharmacology, 2008, Second Edition, pp. 32-33.*
Balasubramanian et al., "G-quadruplex nucleic acids as therapeutic targets", Current Opinion in Chemical Biology, Jun. 2009, pp. 345-353, vol. 13:3.
Burge et al., "Quadruplex DNA: sequence, topology and structure", Nucleic Acids Research, 2006, pp. 5402-5415, vol. 34:19.
Collado et al., "Cellular Senescence in Cancer and Aging", Cell: Leading Edge Review, Jul. 2007, pp. 223-233, vol. 130.
Dai et al., "Structure of the Hybrid-2 type intramolecular human telomeric G-quadruplex in K+ solution: insights into structure polymorphism of the human telomeric sequence", Nucleic Acids Research, Jul. 2007, pp. 4927-4940, vol. 35:15.
Dai et al., "Structure of the intramolecular human telomeric G-quadruplex in potassium solution: a novel adenine triple formation", Nucleic Acids Research, Mar. 2007, pp. 2440-2450, vol. 35:7.
De Lange, "How Telomeres Solve the End-Protection Problem", Science, Nov. 2009, pp. 1-13, vol. 326:5955.
Engelhardt et al., "Does telomere shortening count?", Blood Journal, Aug. 2001, pp. 888-890, vol. 98:3.
Habig et al., "Glutathione S-Transferases: The Final Enzymatic Step in Mercapturic Acid Formation", The Journal of Biological Chemistry, Nov. 1974, pp. 7130-7139, vol. 249:22.
Lowry et al., "Protein Measurement with the Folin Phenol Reagent", The Journal of Biological Chemistry, 1951, pp. 265-275.
Luu et al., "A Phase II Trial of Vorinostat (Suberoylanilide Hydroxamic Acid) in Metastatic Breast Cancer: A California Cancer Consortium Study", Clinical Cancer Research, Nov. 2008, pp. 7138-7142, vol. 14:21.
Marklund et al., "Involvement of the Superoxide Anion Radical in the Autoxidation of Pyrogallol and a Convenient Assay for Superoxide Dismutase", European Journal of Biochemistry, Jun. 1974, pp. 469-474, vol. 47.
Ohkawa et al., "Assay for Lipid Peroxides in Animal Tissues by Thiobarbituric Acid Reaction", Analytical Biochemistry, 1979, pp. 351-358, vol. 95.
Riches et al., "Blood Volume Determination in the Mouse", The Journal of Physiology, 1973, pp. 279-284, vol. 228.
Rodriguez et al., "Rapid Clearance of Human Papillomavirus and Implications for Clinical Focus on Persistent Infections", Journal of the National Cancer Institute, Apr. 2008, pp. 513-517, vol. 100:7.
Saini et al., "Targeting the PI3K/AKT/mTOR and Raf/MEK/ERK pathways in the treatment of breast cancer", Cancer Treatment Reviews, 2013, pp. 935-946, vol. 39.

(Continued)

*Primary Examiner* — Samira Jean-Louis
(74) *Attorney, Agent, or Firm* — The Webb Law Firm

(57) ABSTRACT

A cancer chemotherapeutic agent that is particularly kinase suppressing and/or any other signaling pathway interfering agents and pharmaceutical formulations/compositions involving the same and its process of manufacture is provided. A potential the cancer chemotherapeutic agent is provided which apart from stated anticancer activity as a proven kinase suppressing and/or any other signaling pathway interfering agent could also involve specific potential binding affinity towards the intramolecular G-Quadruplex DNA structure and/or other potential quadruplex forming sequences over duplex DNA structures favors further diverse end use and application including but not limited to antiaging, antiangiogenic, antiproliferative, antitumor, antibiotic, antiviral, antifungal and multiple anticancer therapeutics, and also possesses favorable cytotoxicity values towards uncontrollably proliferative cells by inducing apoptosis irrespective of cells' p53 status, without being cytotoxic to normal cells.

8 Claims, 15 Drawing Sheets

(56) References Cited

PUBLICATIONS

Schipper et al., "A bifunctional allosteric site in the dimer interface of procaspase-3", Biophysical Chemistry, Nov. 2011, pp. 100-109, vol. 159:1.

Yates et al., "Evolution of the cancer genome", Genetics, Nov. 2012, pp. 795-806, vol. 13.

* cited by examiner

CANCER CHEMOTHERAPEUTIC AGENT/FORMULATION, MANUFACTURE AND USE THEREOF

CROSS-REFERENCE TO RELATED APPLICATIONS

This application is the United States national phase of International Application No. PCT/IN2013/000593 filed Sep. 27, 2013, and claims priority to Indian Patent Application No. 1120/KOL/2012 filed Sep. 28, 2012, the disclosures of which are hereby incorporated in their entirety by reference.

REFERENCE TO A SEQUENCING LISTING

The Sequence Listing associated with this application is filed in electronic format via EFS-Web and is hereby incorporated by reference into the specification in its entirety. The name of the text file containing the Sequence Listing is 147881_ST25.txt. The size of the text file is 957 bytes, and the text file was created on Jun. 3, 2015.

FIELD OF INVENTION

The present invention relates to cancer chemotherapeutic agent and, in particular, to cancer chemotherapeutic agent which would be kinase suppressing and/or any other signaling pathway interfering agents and pharmaceutical formulations/compositions involving the same and its process of manufacture thereof. According to a further aspect of the invention the same is directed to a potential the cancer chemotherapeutic agent which apart from stated anticancer activity as a proven kinase suppressing and/or any other signaling pathway interfering agent could also involve specific potential binding affinity towards the intramolecular G-Quadruplex DNA structure and/or other potential quadruplex forming sequences over duplex DNA structures favouring further diverse end use and application including but not limited to antiaging, antiangiogenic, antiproliferative, antitumor, antibiotic, antiviral, antifungal and multiple anticancer therapeutics. The advancement is further targeted to advancements in compounds/agents and identifying its beneficial attributes/selective amounts and pharmaceutical formulation/compositions involving the same which would confirm possessing favourable anti cancerous activity including possessing favourable cytotoxicity values towards uncontrollably proliferative cells by inducing apoptosis irrespective of cells' p53 status, without being cytotoxic to normal cells.

BACKGROUND ART

It is well known in the art that the majority of cytotoxic cancer chemotherapeutic agents act in a relatively indiscriminate manner. The effectiveness of agents such as cyclophosphamide, cis-platinum and adriamycin is a consequence of DNA alkylation, DNA-repair defects and elevated DNA topoisomerase II levels, respectively, in susceptible cancer cell types. However these features, though highly significant for the positive clinical outcomes sometimes seen with these agents, are thus required to be counter-balanced by their high toxicity and generation of resistance mechanisms (Current Opinion in Chemical Biology 2009, 13:345-353).

Alterations of signal transduction pathways leading to uncontrolled cellular proliferation, survival, invasion, and metastases are hallmarks of the carcinogenic process. Protein Kinases are considered to be key regulators of these signal transduction pathways. It is becoming increasingly evident that many of these aberrations converge on a few key pathways involved in cancer cell signal transduction, including the phosphatidylinositol 3-kinase (PI3K)/AKT/mammalian target of rapamycin (mTOR) and the Raf/mitogen-activated and extracellular signal-regulated kinase kinase (MEK)/extracellular signal-regulated kinase (ERK) cascades. Both these pathways play important roles in normal cellular physiology; the carcinogenic process exploits and uses these same pathways to convey constitutively active survival signals to the nucleus. Deregulation of kinase activity has emerged as a major mechanism by which cancer cells evade normal physiological constraints on growth and survival (Cancer Treatment Reviews 39 (2013) 935-946).

Hence, over the past decade the development of anti-cancer drugs has undergone crucial changes. Whereas conventional chemotherapy targets both normal and rapidly dividing cells, newer agents tend to exploit tumor-specific alterations in DNA or in signal transduction pathways.

One of the approach might be to target specific DNA sequences that may combine high target selectivity with the prospect of developing small-drug-like molecules. This entails the targeting of DNA sequence motifs that fold into four-stranded structures called G-quadruplexes. Accumulating evidence has suggested the existence of the G-quadruplex conformation for telomeric DNA sequences both in vitro and in vivo.

Telomeres are DNA-protein complex, which are non-coding highly repetitive sequences located at the 3' end region of the chromosomes consisting of almost 200 nucleotides constituted by tandem repeats of hexanucleotide $(TTAGGG)_n$ and finishes as an over-hanging single strand that provide protection against gene erosion at cell divisions, chromosomal non-homologous end-joining and nuclease attacks. The telomeres have a vital role for life as because of wide functioning with telomere associated proteins, attachment to the nuclear matrix, and higher order chromatin structures (Collado et al., 2007; Campbell, 2012). Conservation of telomeric length is an important biological condition for cell growth (Engelhardt & Finke, 2001; Lange, 2009). Telomeric DNA in vertebrates consists of tandem repeats of hexanucleotide sequence, d(TTAGGG). The G-rich single stranded sequence at the 3'-end of telomeric, DNA can adopt varying tertiary structures including G-Quadruplexes. After each cell division, the telomere sequence gets shortened and that leads to halting of cell division (senescence) and eventually controlled cell death (apoptosis) takes place. Telomerase is the enzyme which functionalizes the addition of hexanucleotide repeats of TTAGGG to the 3'-end of telomere and it's maintenance during normal cell division (mitosis). Unusual over expression of telomerase enzyme engineers massive extension of telomeric ends and brings in anomalous cell proliferation, which causes cancer. Moreover, it has also been demonstrated that in 85% of cancer cells telomerase is over expressed, which prevents natural shortening of telomere and leads to cell proliferation.

Telomeres and telomerase are thus also known to be attractive therapeutic targets in cancer because telomerase is found to be expressed in 80-85% of cancer cells and primary tumours, but not in normal somatic cells.

Telomeres are the main location which forms such crucial functional secondary structures of DNA comprising of a 3'-end region of chromosomes consists of almost 200 nucleotides constituted by tandem repeats of hexanucleotide $(TTAGGG)_n$ and finishes as an over-hanging single strand.

The overhang G-rich repetitive DNA units at 3'-end of telomeres can form various tertiary structures including G-Quadruplex where the guanine bases stack over each other and were stabilized by cyclic Hoogesteen type of hydrogen-bonding (Dai & Carver., 2007; Luu et al., 2008; Burge et al., 2006; Dai & Punchihewa, 2007). The most promising fact of the G-Quadruplex structure is its topology, which cannot be recognized by the single-stranded RNA component of telomerase enzyme. On the contrary it can be recognized by itself as a damage signal of DNA and therefore can invoke apoptosis (Rodriguez et al., 2008).

Though inhibition of telomerase action is an efficient way to tune back cancer cells for natural cell death, one prominent emerging strategy for telomerase inhibition is the stabilization of G-Quadruplex structures of telomeric DNA, thus preventing its availability as a primer for telomerase assisted elongation whereby telomerase activity would be down regulated to bring in apoptosis in cancerous cells.

Quarfloxin (or Quarfloxacin) is known as a fluoroquinolone derivative with antineoplastic activity. Quarfloxin disrupts the interaction between the nucleolin protein and a G-quadruplex DNA structure in the ribosomal DNA (rDNA) template, a critical interaction for rRNA biogenesis that is overexpressed in cancer cells; disruption of this G-quadruplex DNA:protein interaction in aberrant rRNA biogenesis may result in the inhibition of ribosome synthesis and tumor cell apoptosis.

Only very few of the previously investigated compounds in the art have shown specific inhibition of telomerase using nanomolar concentration reflected in their $IC_{50}$ values and therefore, there still remains a need in the art to explore for selective molecules that would have high binding selectivity towards the intramolecular G-Quadruplex structures of telomere over a DNA duplex structure or other potential quadruplex forming sequences in the genome that would effectively stabilize the said G-Quadruplex structures of telomere in minimum effective concentrations at which concentration or dose it would kill more than 50% of cancerous cells but not be cytotoxic to normal cells.

Quite interestingly, there is now a growing body of work that has explored a hypothesis that links the existence of G-quadruplex-forming sequences in promoters of oncogenes including that of kinases. Thus, discovery of Quadruplex stabilizers which bind to promoter regions of oncogenes thereby inhibiting their transcription is quite relevant to cancer therapeutics (Current Opinion in Chemical Biology 2009, 13:345-353).

Further, it is also known in the art that in more than 50% of the cancers, p53 (tumor suppressor protein) is mutated and many existing chemotherapeutic drugs are found to be ineffective in p53 mutated cancers and hence it is also a major challenge of the day to develop anti-cancer agents that can kill cancer cells with non-functional p53.

OBJECTS OF THE INVENTION

Thus the basic object of the present invention is to provide cancer chemotherapeutic agent and in particular kinase suppressing and/or any other signaling pathway interfering agent for killing cancer cells and pharmaceutical formulations/compositions involving the same and its process of manufacture thereof.

Another object of the present invention is directed to identifying cancer chemotherapeutic agent and its selective levels possessing favourable cytotoxicity values towards uncontrollably proliferative cells by inducing apoptosis irrespective of cells' p53 status, without being cytotoxic to normal cells.

One more object of present invention is to provide a cancer chemotherapeutic agent and identifying minimum effective concentrations thereof at which concentration or dose it would kill more than 50% of cancerous cells but not to be cytotoxic to normal cells.

According to another object of present invention the minimum effective concentrations of the chemotherapeutic agent at which concentration or dose it would kill more than 50% of cancerous cells but not to be cytotoxic to normal cells.

Yet another object of the present invention is to provide a pharmaceutical composition comprising cancer chemotherapeutic agent as an active ingredient with pharmaceutically acceptable excipient that could induce apoptosis to favourably prevent uncontrolled proliferation of cells without being cytotoxic to normal cells.

Another object of the present invention is directed to a cancer chemotherapeutic agent/formulations involving the same having high binding affinity towards the intramolecular G-Quadruplex DNA structure and/or other potential quadruplex forming sequences over duplex DNA structures.

Another object of the present invention is to provide a cancer chemotherapeutic agent/formulations involving the same that selectively binds to intramolecular G-quadruplex DNA structure which are present at but not limited to the telomeric region of chromosome, promoter region of oncogenes.

Yet another object of present invention is to provide for cancer chemotherapeutic agent/formulations involving the same having high binding affinity towards said intramolecular G-quadruplex structures irrespective of the cell's p53 (tumor suppressor protein) status.

Another object of the present invention is directed to cancer chemotherapeutic agent/formulations involving the same and in particular to a kinase suppressing and/or any other signaling pathway interfering agents with or without highly selective specific potential binding affinity towards the intramolecular G-Quadruplex DNA structure and/or other potential quadruplex forming sequences over duplex DNA structures favouring diverse end use and application including but not limited to antiaging, antiangiogenic, antiproliferative, antitumor, antibiotic, antiviral, antifungal and multiple cancer therapeutics.

Another object of the present invention is to provide a cancer chemotherapeutic agent and formulations involving the same for inducing apoptosis, having diverse end uses and applications preferably as anti-aging, anti-angiogenic, antiproliferative, anti-tumor, antibiotic, antiviral, antifungal and multiple cancer therapeutics.

Yet another objective of the present invention is to provide a method of treatment for cancer which could be carried out without being cytotoxic to normal cells irrespective of the cell's p53 (tumor suppressor protein) status involving the cancer chemotherapeutic agent for inducing apoptosis for various treatments including aging, angiogenesis, proliferation, tumor, bacterial, viral, fungal and for multiple cancer therapy.

A further object of the present invention is directed to use of an cancer chemotherapeutic agent for inducing apoptosis for various treatments including aging, angiogenesis, proliferation, tumor, bacterial, viral, fungal and for multiple cancer therapy.

Another object of the present invention is to provide use of cancer chemotherapeutic agent for manufacture of a drug for inducing apoptosis by favourably preventing uncontrolled proliferation of cells without being cytotoxic to normal cells irrespective of the cell's p53 (tumor suppressor protein) status.

SUMMARY OF THE INVENTION

Thus the basic aspect of the present invention there is provided an cancer chemotherapeutic agent comprising general formula (I)

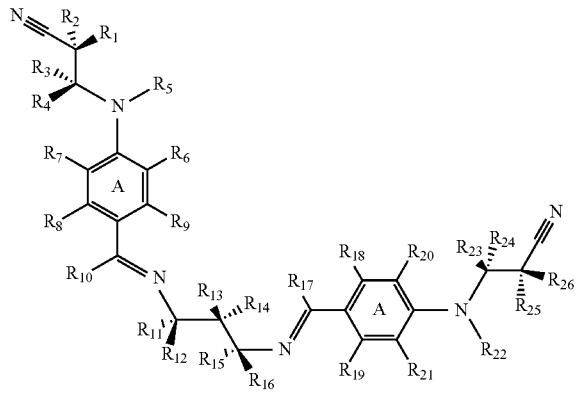

(I)

wherein, $R_1/R_2/R_3/R_4/R_{11}/R_{12}/R_{13}/R_{14}/R_{15}/R_{16}/R_{23}/R_{24}/R_{25}/R_{26}$=Hydrogen, Halo, Acyclic/Cyclic hydrocarbon, Homo or HeteroAromatic, Amino, Amide, Ester, Aldehyde, Ketone, Sulfide, Alkyl halide, Aromatic Halide, Enol, Unsaturated alkenes or alkynes with acid-amide, amine, halo functionalization;

$R_6/R_7/R_8/R_9/R_{18}/R_{19}/R_{20}/R_{21}$=Hydrogen, Halo, Acyclic/Cyclic hydrocarbon, Homo or hetero aromatic group with or without functionalization fused with A (when one group is fused the other group attached to the same side of Aromatic ring does not arise), Amino, Amide, Ester, Aldehyde, Ketone, Sulfide, Alkyl halide, Aromatic Halide, Enol, Unsaturated alkenes or alkynes with acid-amide, amine, halo functionalization;

$R_5/R_{22}$=Methyl, Hydrogen, Halo, Acyclic/Cyclic hydrocarbon, Homo or hetero aromatic group with or without functionalization, Amino, Amide, Ester, Aldehyde, Ketone, Sulfide, Alkyl halide, Aromatic Halide, Enol, Unsaturated alkenes or alkynes with acid-amide, amine, halo functionalization;

$R_{10}/R_{17}$=Hydrogen, Halo, Acyclic/Cyclic hydrocarbon, Homo or hetero aromatic group with or without functionalization, Amino, Amide, Ester, Aldehyde, Ketone, Sulfide, Alkyl halide, Aromatic Halide, Enol, Unsaturated alkenes or alkynes with acid-amide, amine, halo functionalization, in selective cancer chemotherapeutic amounts of 15-40 µM/0.4974 mg/kg-1.3264 mg/kg of for cancer chemotherapeutic activity.

According to another preferred aspect of the present invention there is provided an cancer chemotherapeutic agent comprising Bis(3-[4-({[3-({4-[(2 cyanoethyl)(methyl) amino]benzylidene}amino)propyl]imino}methyl)(methyl) anilino]propanenitrile) compound (M2) of Formula II

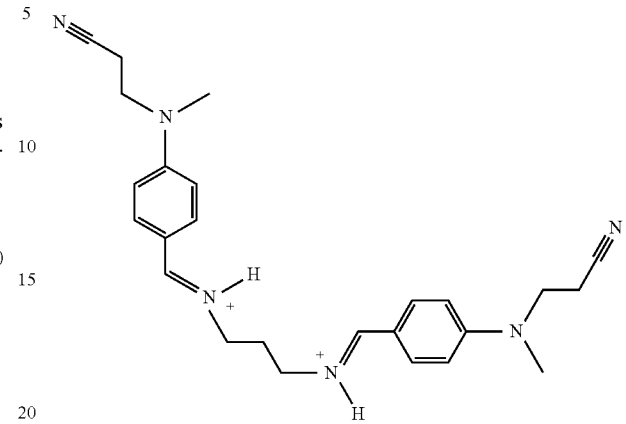

(II)

in selective cancer chemotherapeutic amounts of 15-40 µM/0.4974 mg/kg-1.3264 mg/kg of for cancer chemotherapeutic activity.

According to yet another preferred aspect of the present invention there is provided said cancer chemotherapeutic agent which is a water soluble cancer chemotherapeutic form of molecule of general formula (I) with at least one cationic nitrogen

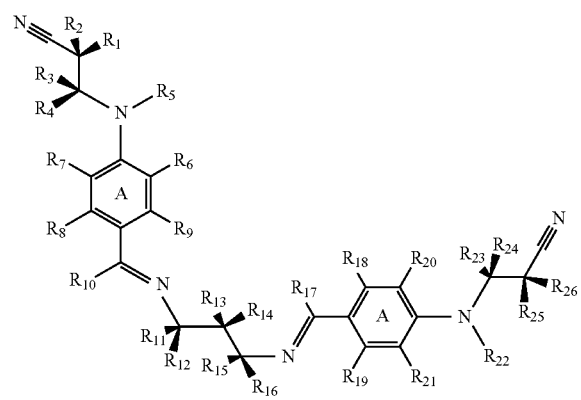

(I)

wherein, $R_1/R_2/R_3/R_4/R_{11}/R_{12}/R_{13}/R_{14}/R_{15}/R_{16}/R_{23}/R_{24}/R_{25}/R_{26}$=Hydrogen, Halo, Acyclic/Cyclic hydrocarbon, Homo or HeteroAromatic, Amino, Amide, Ester, Aldehyde, Ketone, Sulfide, Alkyl halide, Aromatic Halide, Enol, Unsaturated alkenes or alkynes with acid-amide, amine, halo functionalization;

$R_6/R_7/R_8/R_9/R_{18}/R_{19}/R_{20}/R_{21}$=Hydrogen, Halo, Acyclic/Cyclic hydrocarbon, Homo or hetero aromatic group with or without functionalization fused with A (when one group is fused the other group attached to the same side of Aromatic ring does not arise), Amino, Amide, Ester, Aldehyde, Ketone, Sulfide, Alkyl halide, Aromatic Halide, Enol, Unsaturated alkenes or alkynes with acid-amide, amine, halo functionalization;

$R_5/R_{22}$=Methyl, Hydrogen, Halo, Acyclic/Cyclic hydrocarbon, Homo or hetero aromatic group with or without functionalization, Amino, Amide, Ester, Aldehyde, Ketone, Sulfide, Alkyl halide, Aromatic Halide, Enol, Unsaturated alkenes or alkynes with acid-amide, amine, halo functionalization;

$R_{10}/R_{17}$=Hydrogen, Halo, Acyclic/Cyclic hydrocarbon, Homo or hetero aromatic group with or without functionalization, Amino, Amide, Ester, Aldehyde, Ketone, Sulfide, Alkyl halide, Aromatic Halide, Enol, Unsaturated alkenes or alkynes with acid-amide, amine, halo functionalization, having cancer chemotherapeutic activity.

According to yet another preferred aspect of the present invention there is provided said cancer chemotherapeutic agent which is a water soluble form of the molecule of general formula (I) with at least one cationic nitrogen.

According to yet another preferred aspect of the present invention there is provided said cancer chemotherapeutic agent wherein the general formula (I) comprise two protonated nitrogens having the structures as represented hereunder

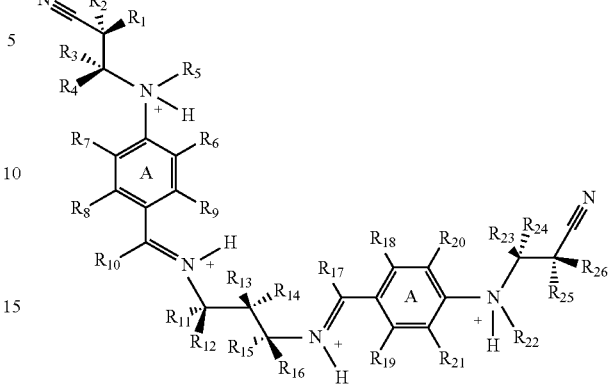

(IC)

According to yet another preferred aspect of the present invention there is provided said cancer chemotherapeutic agent having the structure as represented hereunder as formula II

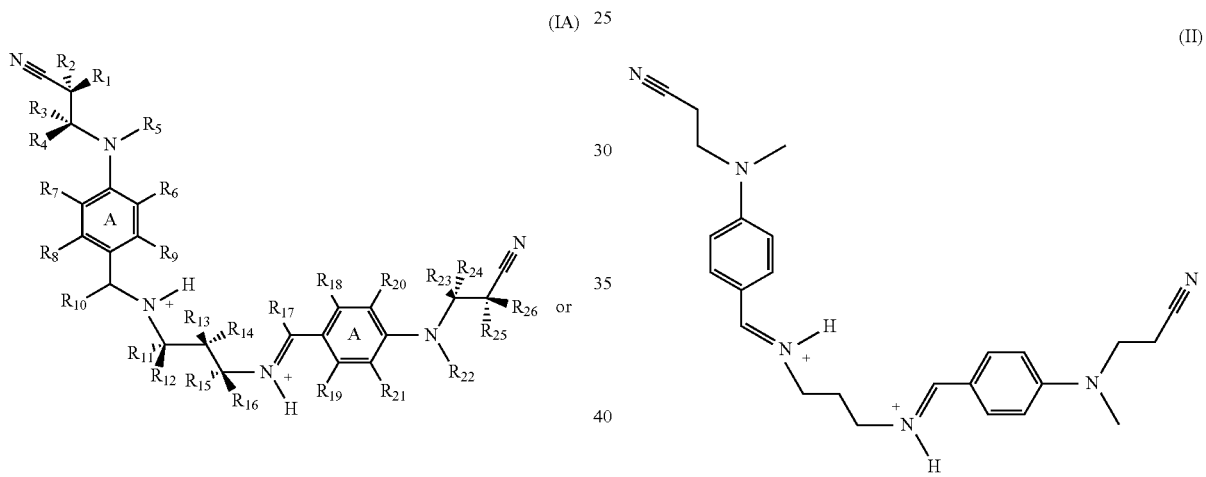

(IA)

(II)

(IB)

According to yet another preferred aspect of the present invention there is provided a process for the preparation of an cancer chemotherapeutic agent having general formula (I) in water soluble form comprising the steps of
(i) adding a cation to the molecule of general formula I in amounts such as to favour cationic linkage to atleast one nitrogen;
(ii) optionally if required, adjusting the pH to obtain therefrom said soluble form of said agent.

According to yet another preferred aspect of the present invention there is provided a process for the preparation of an cancer chemotherapeutic agent wherein said step (i) involves adding acids to protonate atleast one nitrogen; wherein said step (ii) involves adjustment of the pH to about 7 by addition of sodium or potassium bi carbonate to obtain protonated water soluble form preferably compound of Formula II.

According to yet another preferred aspect of the present invention there is provided a process wherein the acids include inorganic acids selected from HCl, $H_2SO_4$ or $HNO_3$.

According to yet another preferred aspect of the present invention there is provided a process comprising providing said agents in selective amounts of 15-40 µM/0.4974 mg/kg-1.3264 mg/kg of for cancer chemotherapeutic activity.

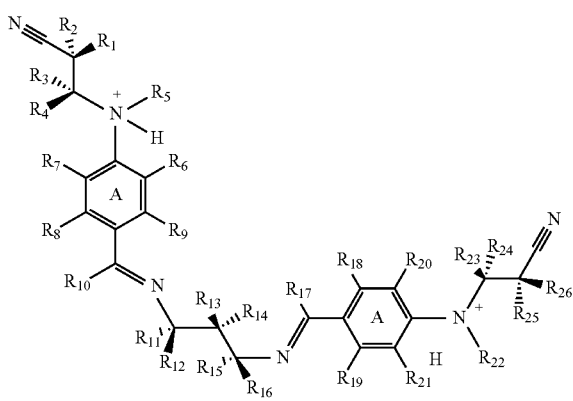

According to yet another preferred aspect of the present invention there is provided said cancer chemotherapeutic agent wherein the general formula (I) with four protonated nitrogens has the structure as represented hereunder According to yet another preferred aspect of the present invention there is provided a pharmaceutical formulation/composition comprising:

(i) An cancer chemotherapeutic agent comprising general formula (I)

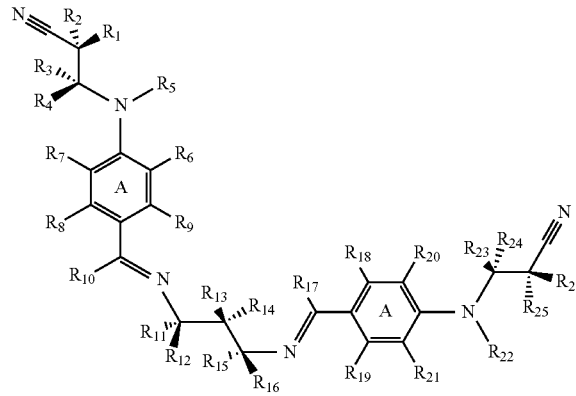

wherein, $R_1/R_2/R_3/R_4/R_{11}/R_{12}/R_{13}/R_{14}/R_{15}/R_{16}/R_{23}/R_{24}/R_{25}/R_{26}$=Hydrogen, Halo, Acyclic/Cyclic hydrocarbon, Homo or HeteroAromatic, Amino, Amide, Ester, Aldehyde, Ketone, Sulfide, Alkyl halide, Aromatic Halide, Enol, Unsaturated alkenes or alkynes with acid-amide, amine, halo functionalization;

$R_6/R_7R_8/R_9/R_{18}/R_{19}/R_{20}/R_{21}$=Hydrogen, Halo, Acyclic/Cyclic hydrocarbon, Homo or hetero aromatic group with or without functionalization fused with A (when one group is fused the other group attached to the same side of Aromatic ring does not arise), Amino, Amide, Ester, Aldehyde, Ketone, Sulfide, Alkyl halide, Aromatic Halide, Enol, Unsaturated alkenes or alkynes with acid-amide, amine, halo functionalization;

$R_5/R_{22}$=Methyl, Hydrogen, Halo, Acyclic/Cyclic hydrocarbon, Homo or hetero aromatic group with or without functionalization, Amino, Amide, Ester, Aldehyde, Ketone, Sulfide, Alkyl halide, Aromatic Halide, Enol, Unsaturated alkenes or alkynes with acid-amide, amine, halo functionalization;

$R_{10}/R_{17}$=Hydrogen, Halo, Acyclic/Cyclic hydrocarbon, Homo or hetero aromatic group with or without functionalization, Amino, Amide, Ester, Aldehyde, Ketone, Sulfide, Alkyl halide, Aromatic Halide, Enol, Unsaturated alkenes or alkynes with acid-amide, amine, halo functionalization, in selective cancer chemotherapeutic amounts of 15-40 µM/0.4974 mg/kg-1.3264 mg/kg of for cancer chemotherapeutic activity;

(ii) pharmaceutically acceptable excipients/carriers thereof.

According to yet another preferred aspect of the present invention there is provided a pharmaceutical formulation/composition comprising said cancer chemotherapeutic agent comprising Bis(3-[4-({[3-({4-[(2 cyanoethyl)(methyl) amino]benzylidene}amino)propyl]imino}methyl)(methyl) anilino]propanenitrile) compound of Formula II

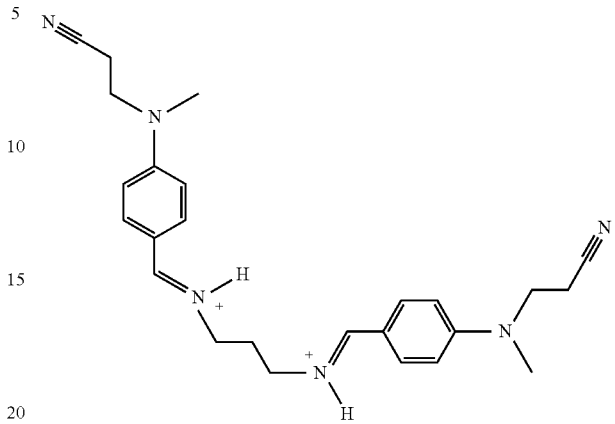

in selective cancer chemotherapeutic amounts of 15-40 µM/0.4974 mg/kg-1.3264 mg/kg of for cancer chemotherapeutic activity.

According to yet another preferred aspect of the present invention there is provided a pharmaceutical formulation/composition wherein said cancer chemotherapeutic agent is a water soluble form of the molecule of general formula (I) with at least one cationic nitrogen

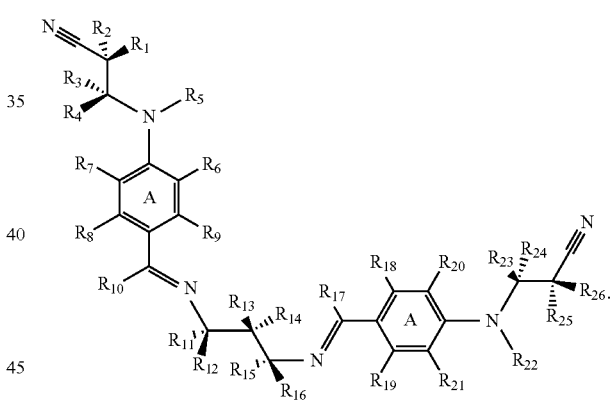

wherein, $R_1/R_2/R_3/R_4/R_{11}/R_{12}/R_{13}/R_{14}/R_{15}/R_{16}/R_{23}/R_{24}/R_{25}/R_{26}$=Hydrogen, Halo, Acyclic/Cyclic hydrocarbon, Homo or HeteroAromatic, Amino, Amide, Ester, Aldehyde, Ketone, Sulfide, Alkyl halide, Aromatic Halide, Enol, Unsaturated alkenes or alkynes with acid-amide, amine, halo functionalization;

$R_6/R_7/R_8/R_9/R_{18}/R_{19}/R_{20}/R_{21}$=Hydrogen, Halo, Acyclic/Cyclic hydrocarbon, Homo or hetero aromatic group with or without functionalization fused with A (when one group is fused the other group attached to the same side of Aromatic ring does not arise), Amino, Amide, Ester, Aldehyde, Ketone, Sulfide, Alkyl halide, Aromatic Halide, Enol, Unsaturated alkenes or alkynes with acid-amide, amine, halo functionalization;

$R_5/R_{22}$=Methyl, Hydrogen, Halo, Acyclic/Cyclic hydrocarbon, Homo or hetero aromatic group with or without functionalization, Amino, Amide, Ester, Aldehyde, Ketone, Sulfide, Alkyl halide, Aromatic Halide, Enol, Unsaturated alkenes or alkynes with acid-amide, amine, halo functionalization;

$R_{10}/R_{17}$=Hydrogen, Halo, Acyclic/Cyclic hydrocarbon, Homo or hetero aromatic group with or without functionalization, Amino, Amide, Ester, Aldehyde, Ketone, Sulfide, Alkyl halide, Aromatic Halide, Enol, Unsaturated alkenes or alkynes with acid-amide, amine, halo functionalization, having cancer chemotherapeutic activity.

According to yet another preferred aspect of the present invention there is provided a pharmaceutical formulation/composition wherein said cancer chemotherapeutic agent is a water soluble form of the molecule of general formula (I) with at least one cationic nitrogen.

According to yet another preferred aspect of the present invention there is provided a pharmaceutical formulation/composition wherein said cancer chemotherapeutic agent is of general formula (I) comprise two protonated nitrogens having the structures as represented hereunder

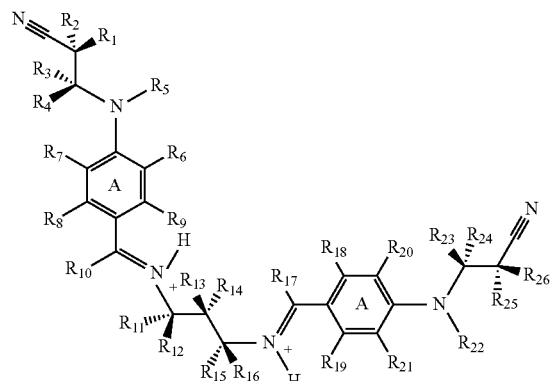

According to yet another preferred aspect of the present invention there is provided a pharmaceutical formulation/composition wherein said cancer chemotherapeutic agent is of general formula (I) with four protonated nitrogens has the structure as represented hereunder

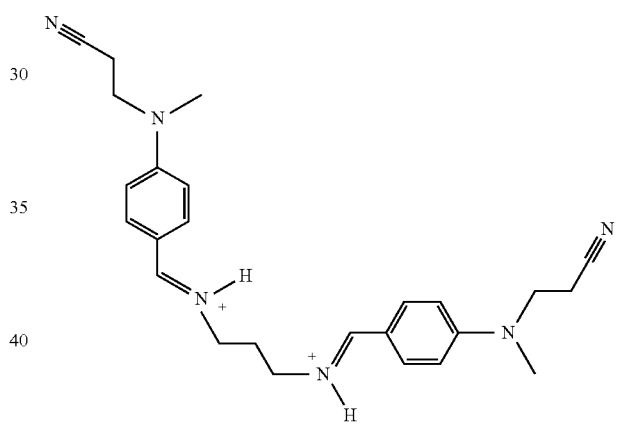

According to yet another preferred aspect of the present invention there is provided a pharmaceutical formulation/composition wherein said cancer chemotherapeutic agent comprises compound of Formula II having structure as represented hereunder as formula II According to yet another preferred aspect of the present invention there is provided a pharmaceutical formulation/composition as claimed in anyone of claims 14 to 18 in forms selected from solid formulation in form of tablets, suspensions, syrups, dispersions, injectables.

According to yet another preferred aspect of the present invention there is provided a method for manufacture of a pharmaceutical formulation/composition comprising:
selectively providing cancer chemotherapeutic amounts of 15-40 μM/0.4974 mg/kg-1.3264 mg/kg of for cancer chemotherapeutic activity.

According to yet another preferred aspect of the present invention there is provided a method of inducing apoptosis to favourably prevent uncontrolled proliferation of cells comprising administering said selective cancer chemotherapeutic amounts of 15-40 NM/0.4974 mg/kg-1.3264 mg/kg of said compound of Formula I or Formula II.

According to yet another preferred aspect of the present invention there is provided a method which is carried out without being cytotoxic to normal cells irrespective of the cell's p53 (tumor suppressor protein) status involving the said cancer chemotherapeutic agent of general Formula (I) or Formula II.

According to yet another preferred aspect of the present invention there is provided a method of inducing apoptosis for various treatments including aging, angiogenesis, proliferation, tumor, bacterial, viral, fungal and for multiple cancer therapy.

According to yet another preferred aspect of the present invention there is provided use of an cancer chemotherapeutic agent of general Formula (I) or Formula II in cancer chemotherapeutic effective amounts of 15-40 μM/0.4974 mg/kg-1.3264 mg/kg of to selectively carry out anyone or more of stabilize G-Quadruplex structures in cancer cells down regulating telomerase, oncogenic activities or suppressing kinase expression.

According to yet another preferred aspect of the present invention there is provided use of an cancer chemotherapeutic agent of general Formula (I) or Formula II in effective amounts of 15-40 μM/0.4974 mg/kg-1.3264 mg/kg of for manufacture of a drug for inducing apoptosis by favourably preventing uncontrolled proliferation of cancer cells without being cytotoxic to normal cells irrespective of the cell's p53 (tumor suppressor protein) status.

According to yet another preferred aspect of the present invention there is provided the cancer chemotherapeutic form of compound of Formula I or Formula II or its derivatives for treatment of for various treatments including aging, angiogenesis, proliferation, tumor, bacterial, viral, fungal and for multiple cancer therapy including lung, breast, liver, gastric cancer, sarcoma, cervical cancer etc. comprising both wild type and mutated p53 wherein the dosage of the compound is most effective at the concentration between 10-25 μM in and around the or tissue fluid.

According to yet another preferred aspect of the present invention there is provided the method further comprising treatment with an intraperitonial dose in between 15 μM (0.4974 mg/kg) and 40 μM (1.3264 mg/kg)

The details of the invention, its objects and advantages are explained hereunder in greater detail in relation to the following non-limiting exemplary illustrations including the following accompanying figures:

BRIEF DESCRIPTION OF ACCOMPANYING FIGURES

FIG. 1 illustrates effect of M2 on A) Tumor Cell Count, B) Tumor weight C) percentage inhibition in cell count & D) percentage inhibition in tumor weight. (A) Cells from tumor tissue were harvested and a single cell suspension was prepared. Cell count was determined by the Trypan Blue exclusion method; B) tumors were excised 4 weeks after subcutaneous injection of sarcoma-180 cells and weighed. Data represented in bar diagrams of mean±SD of three independent experiments;

FIG. 2 illustrates the size of solid tumours in (a) Sarcoma control (b) Cyclophosphamide treated tumor and (c) M2 treated tumor FIG. 3 illustrates flowcytometric detection of the effect of M2 on S-180 cell cycle phase distribution. S-180 cell from tumor-bearing treated and untreated mice were fixed and nuclear DNA was labeled with PI. Cell cycle phase distribution of S-180 nuclear DNA was determined by single label flowcytometry. Histogram display of DNA content (x-axis, PI-fluorescence) versus counts (y-axis) has been shown. Tumor cell cycle analysis reveals that M2-treatment reduced the proliferative phase and increased the hypoploidy percentage as compared to untreated groups;

FIG. 4 illustrates effect of M2 on the induction of apoptosis in tumor cells as determined by alakaline single cell gel electrophoresis (Comet Assay). A) The bar graphs represent percentage comet cells per field of the slide studied in different experimental groups. B) Representative slides showing comet cells in different experimental groups. DNA fragmentation has clearly increased by M2 treatment as can be seen by the increased 'comet length' as well as increased number of comet cells in the treated groups in comparison to the sarcoma control group;

Figure 7:
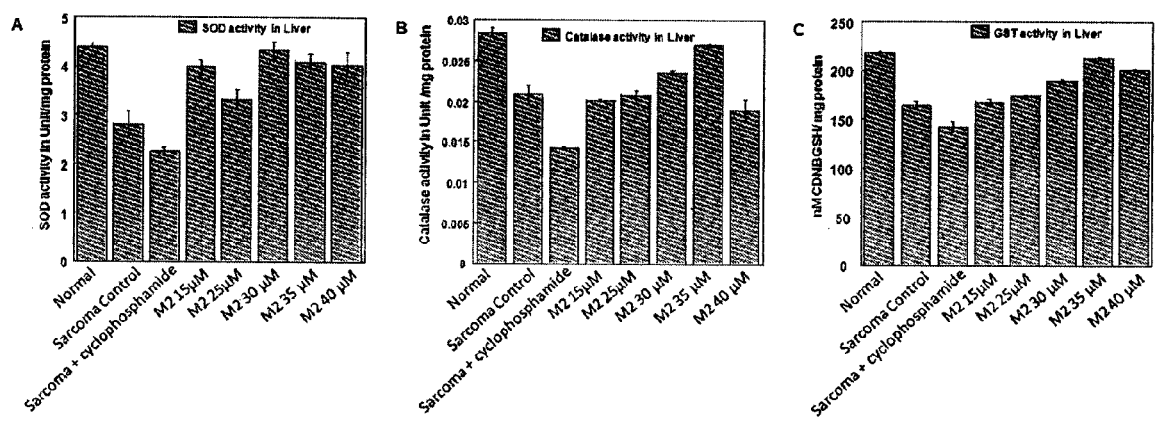
Figure 8:
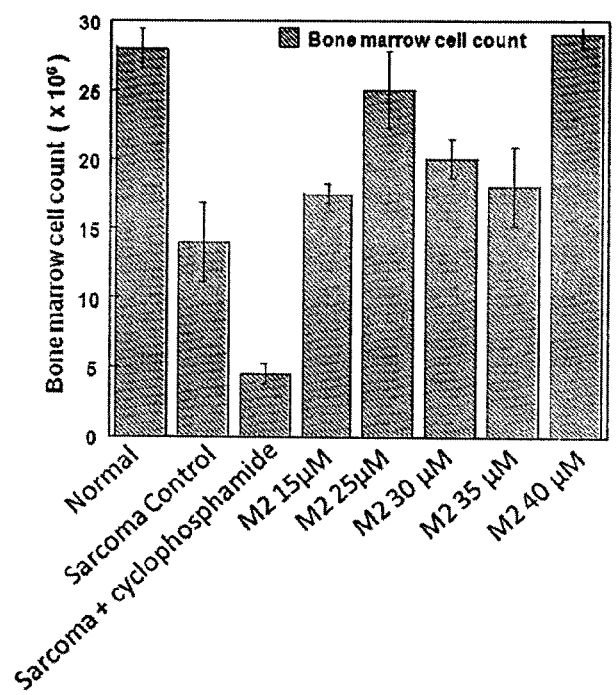
Figure 9:
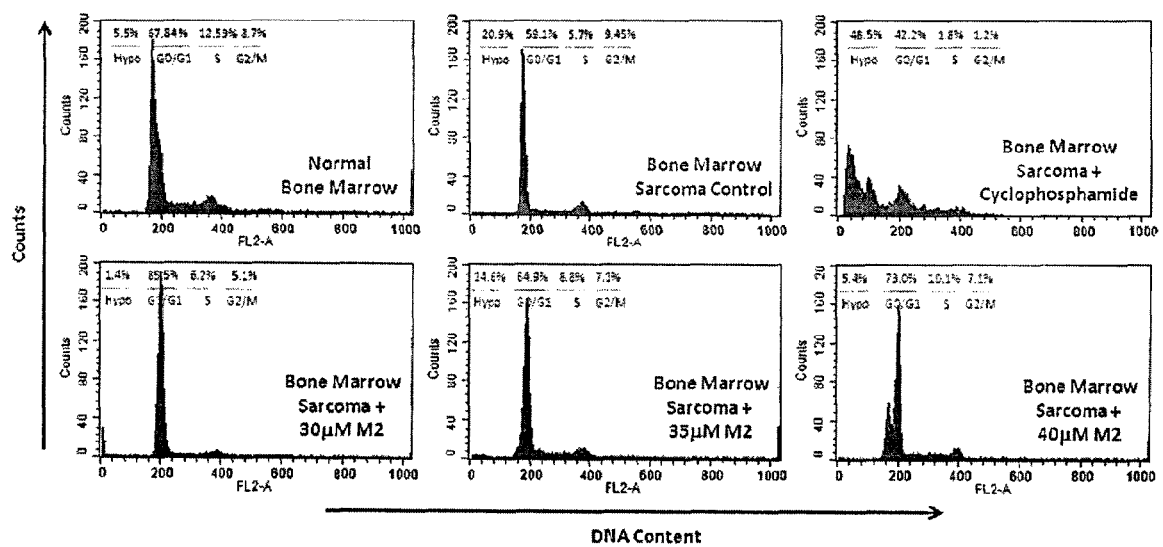
Figure 10:
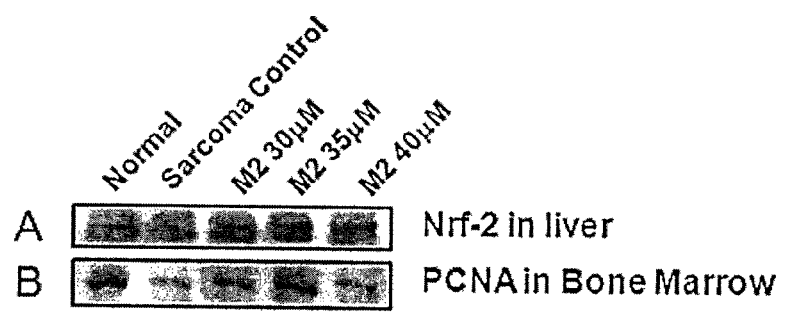

FIG. 7 illustrates effect of M2 on hepatic anti-oxidant enzymes. A) SOD activity was measured based on pyrogallol auto oxidation inhibition and expressed as unit/mg of protein. B) CAT activity in was assessed by measuring the breakdown of $H_2O_2$ spectrophotometrically at 240 nm. C) Hepatic GST activity was measured by determining the increase in absorbance at 340 nm with 1-chloro-2,4-dinitrobenzene (CDNB) as the substrate. Data represented in bar diagrams of mean±SD of three independent experiments;

FIG. 8 illustrates effect of M2 on bone marrow cell count. A single cell suspension of the bone marrow was made with repeated aspiration of the femur (1 cm) excised from mice of all the experimental groups and cell count was determined by Trypan Blue exclusion method. Data represented in bar diagrams of mean±SD of three independent experiments;

FIG. 9 illustrates effect of M2 on bone marrow cell cycle phase distribution. Bone Marrow cells from mice were fixed and nuclear DNA was labeled with PI. Cell cycle phase distribution of bone marrow nuclear DNA was determined by single label flowcytometry. Histogram display of DNA content (x-axis, PI-fluorescence) versus counts (y-axis) has been shown;

FIG. 10 illustrates effect of M2 on protein expressions. A) Liver tissue cell lysates were subjected to western blot analysis with anti-Nrf 2 antibody in all the experimental groups. B) Cell lysates from bone marrow was subjected to Western Blot analyses to study the expression of PCNA of all the experimental groups. Equal loading of protein in the lanes was confirmed by GAPDH.

Figure 11:
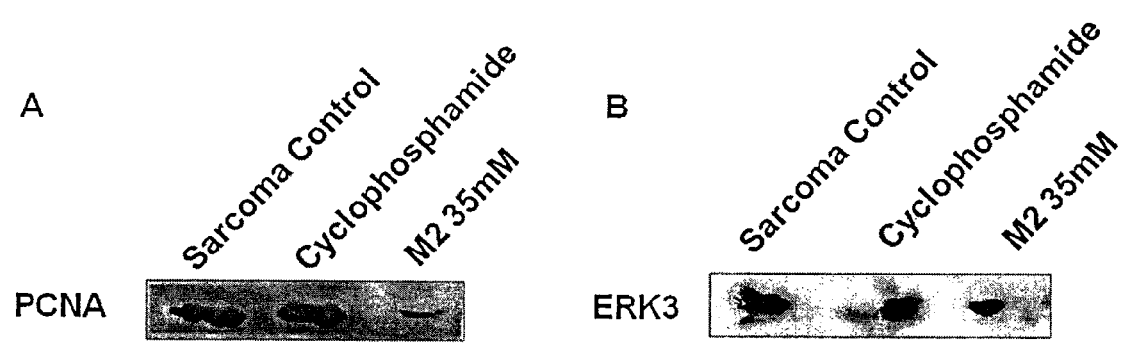

FIG. 11 illustrates the Effect of M2 on Tumor tissue proliferation marker and Kinase. Cell lysates from tumor tissue was subjected to Western Blot analyses to study the expression of A) PCNA & B) ERK of the experimental groups mentioned.

Figure 12:
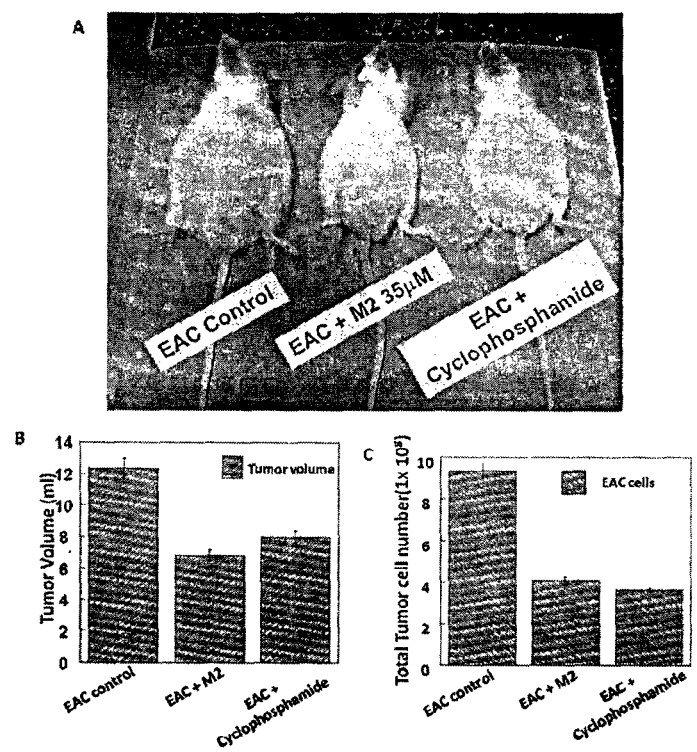

FIG. 12 Illustrates the antitumor effect of M2 against EAC tumor model. Treatment with M2 was able to significantly reduce Tumor volume A) Picture of the untreated EAC bearing mice compared with treatment with M2 or cyclophosphamide. B) mice were sacrified and peritoneal fluid was measured in measuring cylinder 4 weeks after intraperitoneal injection of EAC cells. C) Tumor cell count. Cells from peritoneal fluid were harvested and a single cell suspension was prepared. Cell count was determined by the Trypan Blue exclusion method. Data represented in bar diagrams of mean±SD of three independent experiments.

Figure 13:
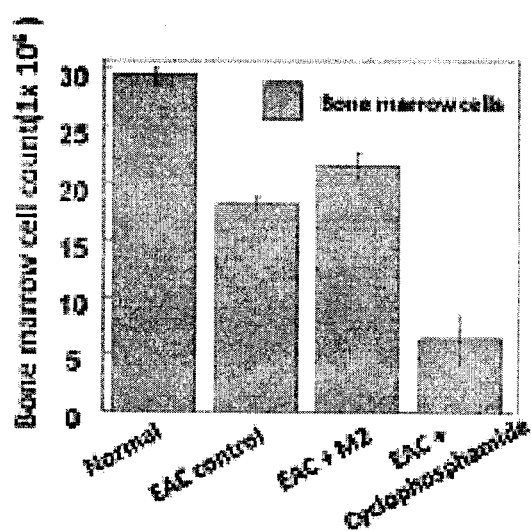

FIG. 13 illustrates the effect of M2 on bone marrow cell count in EAC tumor bearing mice. A single cell suspension of the bone marrow was made with repeated aspiration of the femur (1 cm) excised from mice of all the experimental groups and cell count was determined by Trypan Blue exclusion method. Data represented in bar diagrams of mean±SD of three independent experiments.

Figure 14:
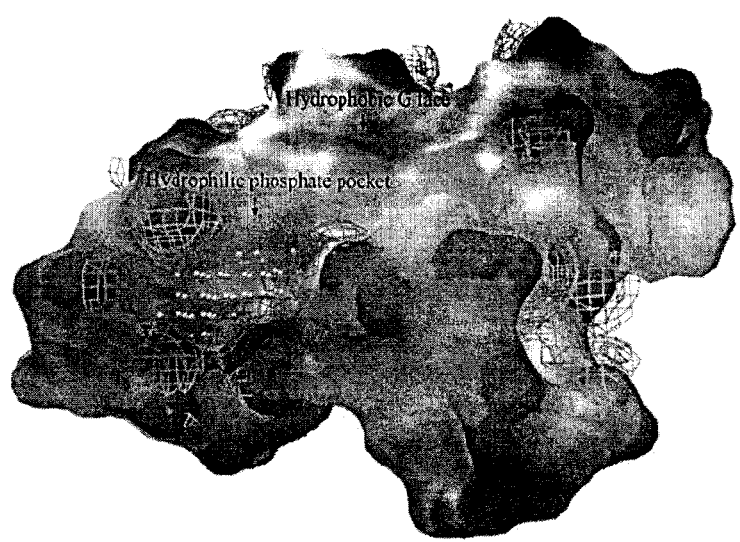
Figure 15:
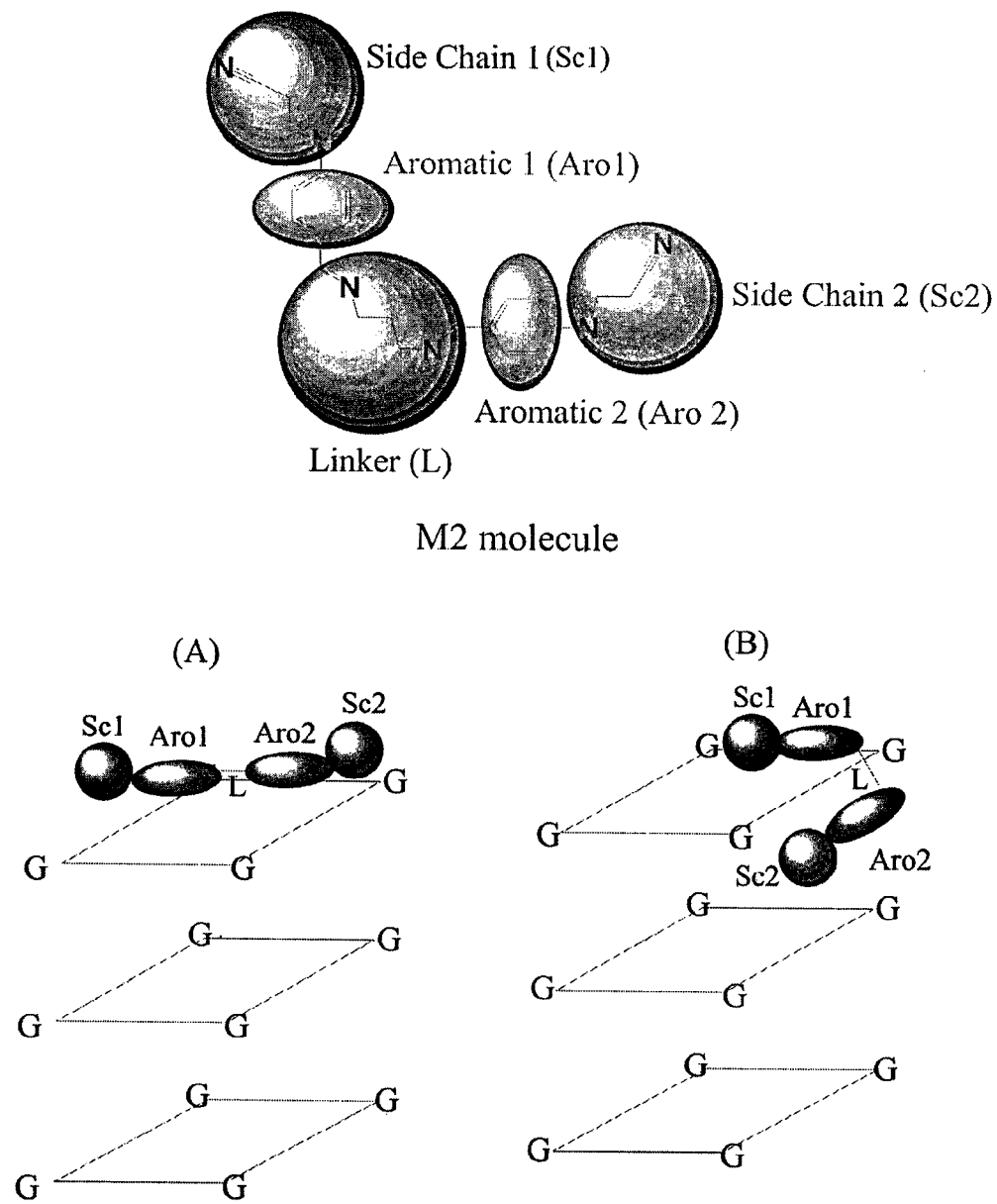

FIG. 14 illustrates the binding sites of selective G-quadruplex (2LD8.pdb) structure showing the hydrophilic loop regions and the central hydrophobic core formed by the co-facial Guanine residues;

FIG. 15 illustrates schematic representation of ligand M2, binding to G-Quadruplex, TAGGG(TTAGGG)$_3$(2LD8.pdb); Sc1, Sc2 stabilize the phosphate backbone; Aro1, Aro2 stabilize the Guanine rich G-face with stacking; Linker stabilizes the Guanine rich G-face with hydrogen bonding.

Figure 16:
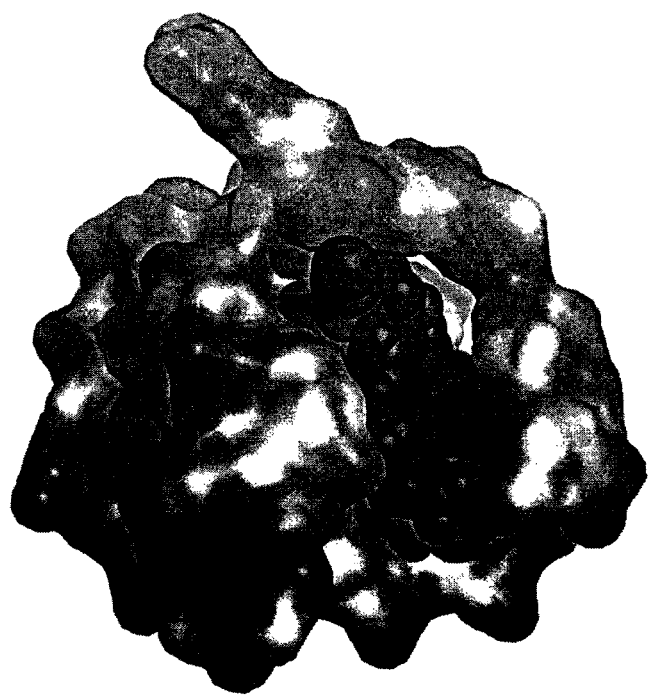
Figure 17:
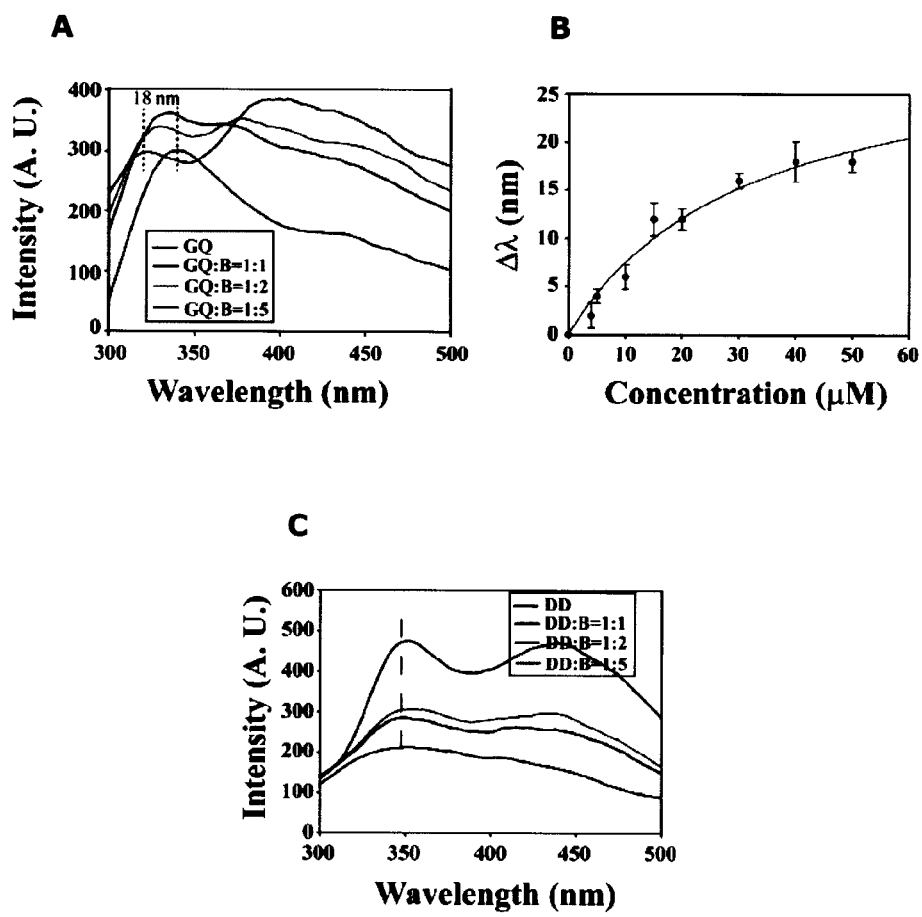

FIG. 16 illustrates M2 bound to c-Myc quadruplex;

FIG. 17 illustrates Fluorescence emission spectra of G-Quadruplex (represented here as GQ) in presence of M2 (graph A). Determination of G-Quadruplex binding affinity of M2 (graph B) following the changes in emission maxima (Amax) of G-Quadruplex in the context of ligand concentrations. Fluorescence emission spectra of GC rich duplex DNA (represented here as DD) in presence of M2 (graph C);

DETAILED DESCRIPTION OF INVENTION

As discussed hereinbefore the present invention in an embodiment provides in effective amounts of 15-40 μM/0.4974 mg/kg-1.3264 mg/kg of body weight of an cancer chemotherapeutic/kinase suppressing and/or any other signaling pathway interfering agent (I) that would kill cancer cells irrespective of the cellular p53 status and induce apoptosis to prevent uncontrolled proliferation of cancerous cells without being cytotoxic towards normal cells which indicate its diverse end use and application in antiaging, antiangiogenic, antiproliferative, antitumor, antibiotic, antiviral, antifungal and multiple anticancer therapeutics.

The present invention in another embodiment provides a soluble form of cancer chemotherapeutic agent (I) wherein the molecule of general formula (I) is with at least one cationic nitrogen to prevent uncontrolled proliferation of cancerous cells without being cytotoxic towards normal cells.

In both the above embodiments the cancer chemotherapeutic agent comprising formula (I) for the present invention wherein (I) has the general formula:

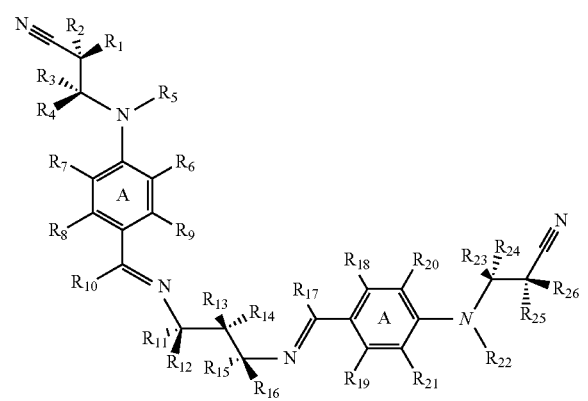

(I)

wherein, $R_1/R_2/R_3/R_4/R_{11}/R_{12}/R_{13}/R_{14}/R_{15}/R_{16}/R_{23}/R_{24}/R_{25}/R_{26}$=Hydrogen, Halo, Acyclic/Cyclic hydrocarbon, Homo or HeteroAromatic, Amino, Amide, Ester, Aldehyde, Ketone, Sulfide, Alkyl halide, Aromatic Halide, Enol, Unsaturated alkenes or alkynes with (acid-amide, amine, halo functionalization);

$R_6/R_7/R_8/R_9/R_{18}/R_{19}/R_{20}/R_{21}$=Hydrogen, Halo, Acyclic/Cyclic hydrocarbon, Homo or hetero aromatic group with or without functionalization fused with A (when one group is fused the other group attached to the same side of Aromatic ring does not arise), Amino, Amide, Ester, Aldehyde, Ketone, Sulfide, Alkyl halide, Aromatic Halide, Enol, Unsaturated alkenes or alkynes with (acid-amide, amine, halo functionalization);

$R_5/R_{22}$=Methyl, Hydrogen, Halo, Acyclic/Cyclic hydrocarbon, Homo or hetero aromatic group with or without functionalization, Amino, Amide, Ester, Aldehyde, Ketone, Sulfide, Alkyl halide, Aromatic Halide, Enol, Unsaturated alkenes or alkynes with (acid-amide, amine, halo functionalization);

$R_{10}/R_{17}$=Hydrogen, Halo, Acyclic/Cyclic hydrocarbon, Homo or hetero aromatic group with or without functionalization, Amino, Amide, Ester, Aldehyde, Ketone, Sulfide, Alkyl halide, Aromatic Halide, Enol, Unsaturated alkenes or alkynes with (acid-amide, amine, halo functionalization).

The general formula (I) comprise two protonated nitrogens having the structures as represented hereunder

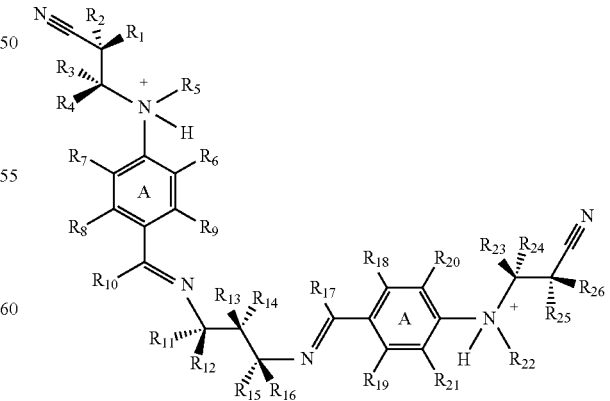

(IA)

(IB)

the general formula (I) with four protonated nitrogens has the structure as represented hereunder

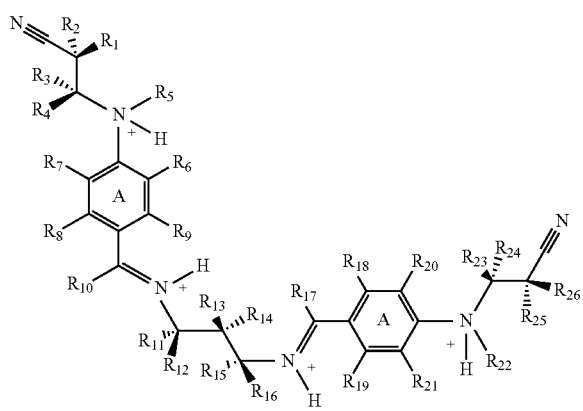

The water soluble form of formula (I) are obtained through (i) adding a cation to the molecule of general formula I to favour cationic linkage to atleast one nitrogen; (ii) optionally, adjusting the pH to obtain therefrom said soluble form of said G-quadruplex stabilizing agent.

The present invention also provides a pharmaceutical composition comprising soluble form of (I) as an active ingredient with pharmaceutically acceptable excipient which include acceptable salts, esters, sucrose, mannitol, gelatin capsules etc. The pharmaceutically acceptable salts include carboxylate salts, amino acid addition salts. The pharmaceutical composition comprising soluble form of (I) as an active ingredient used for inducing apoptosis to favourably prevent uncontrolled proliferation of cells without being cytotoxic to normal cells. The pharmaceutical composition can be provided into different forms including tablets, suspensions, syrups, dispersion. Dispersions can also be prepared in glycerol, liquid polyethylene glycols, triacetin, and mixtures thereof.

Various embodiments of the present invention are described below. The present invention encompasses other compounds having formula I and is not limited to the specific combinations of substituents described in various embodiments below.

The water soluble form of M2 is obtained through lowering of pH and protonation with the help of acids and then adjusting the pH with sodium or potassium bicarbonate to 7.0. The lowering of pH and protonation can be done using acids selected from HCl, $H_2SO_4$, $HNO_3$ etc.

The above said water soluble cancer therapeutic agents/formulations comprising M2 of the present invention and the molecular frameworks derived out of the said molecule is found to possess said cancer therapeutic activity under minimum effective concentrations at which concentration or dose it effectively kills more than 50% of cancerous cells and are also advantageously not cytotoxic to normal cells, wherein such selective strong binding is irrespective of the cell's p53 (tumor suppressor protein) status.

In another preferred embodiment of the present invention said water soluble cancer chemotherapeutic/kinase suppressors agent/formulations involving the same also possesses favourable cytotoxicity values independent of the cell's p53 status set to favourably prevent uncontrolled proliferation of cells. It is known that in more than 50% of the cancers, p53 is mutated and many existing chemotherapeutic drugs are found to be ineffective in p53 mutated cancers. It is a major challenge, thus, to develop anti-cancer agents that can kill cancer cells with non-functional p53. As evident from the examples, this novel compound M2 in the range of 15-40 µM/0.4974 mg/kg-1.3264 mg/kg of body weight and the water soluble form of M2, Form II have a great potential as an anti-cancer agent whose cytotoxicity is not dependent on the cell's p53 status.

The advancement is illustrated hereunder in further detail in relation to the following non-limiting exemplary illustrations as hereunder:

The anti-proliferative effect of water soluble M2 which can be extended as anti-tumor activity are also studied in vitro and in vivo following the procedures as mentioned hereunder:

Example I: Protonation of M2 to Make it Soluble

M2 is not soluble in water at pH 7.0 in its ordinary form. When it is protonated using 0.1M HCl, it gets solubilized. Just after that the pH is adjusted by addition of sodium or potassium bi carbonate to keep the soluble form of M2 at pH 7.0. The protonation is very much important to generate protonated M2 (form II) which is a new species that is soluble in water and used for other experimental studies.

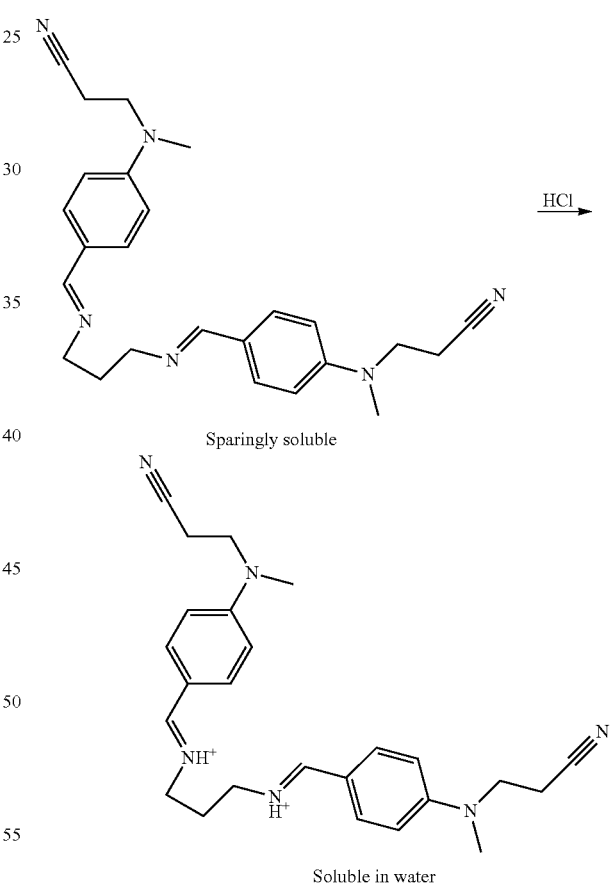

All the subsequent examples cited below were performed with water soluble form of M2.

Example II: In Vitro Study (A) Cytotoxicity Studies of M2 Against Human Peripheral Blood Mononuclear Cells (PBMC).

The toxicity of M2 was tested against human PBMC. Peripheral blood mononuclear cells (PBMC) were isolated from normal human blood and were maintained in RPMI supplemented with 10% FBS, 100 µg/ml streptomycin and 50 units/ml penicillin, at 37° C. in a humidified incubator containing 5% $CO_2$. For experiments, required numbers of cells ($10^6$) were plated with 2% serum and then the experiments were performed where a series of concentrations of M2 was administered in human PBMC and after 12 hours, cell viability was assessed. The doses that were tested ranged between $0.5433 \times 10^{-7}$ µM to 35 µM. Out of these, 35 µM (which is the highest dose used) concentration was found to be toxic as ~25% PBMC could not survive this treatment.

During the next phase, some doses from the previous set of experiments were selected and cytotoxicity assay was once again carried out with these selected doses against human PBMC. This time a concentration ranging between 0.1 to 30 µM were selected. Once again doses 0.1 to 25 µM were found to have negligible effect on the viability of human PBMC. However, the highest dose (30 µM) was found to exert cytotoxic effect on human PBMC (Table 1). Apart from cell viability assay, the genotoxicity of the different concentrations of compound against human PBMC was also tested by alkaline single cell gel electrophoresis assay. In accordance with the cytotoxicity data, there was no significant comet formation with any of the doses except the 30 µM dose. Survivability of the cells at varying concentrations of the compound was tabulated as mean±Standard Deviation of five independent experiments.

TABLE 1

| | | Dose | | | | | | | |
|---|---|---|---|---|---|---|---|---|---|
| | | Vehicle Control | | | | | | | |
| | 0.0 | (0.51 mM HCl) | 30 µM | 25 µM | 20 µM | 15 µM | 10 µM | 5 µM | 1 µM |
| Total Cell Count (% survival) | 100% | 98.67 ± 1.21 | 77.67 ± 3.44 | 85.17 ± 1.94 | 87.33 ± 1.97 | 88.83 ± 1.47 | 88.67 ± 1.75 | 89.50 ± 1.05 | 90.67 ± 2.16 |

(B) Cytotoxicity Studies of M2 Against Cancer Cell Lines with Wild Type and Mutated p53.

Cancer cell lines with functional or disrupted p53 expression were maintained in ATCC recommended culture media supplemented with 10% FBS, 100 µg/ml streptomycin and 50 units/ml penicillin, at 37° C. in a humidified incubator containing 5% $CO_2$. For experiments, cells ($10^6$) were plated with 2% serum and then the required experiments were performed. On the basis of the above study, three doses (15, 20, 25 µM) were selected and the effects of the compound were tested against lung, liver and breast cancer cell lines having wild type p53. Simultaneously, the effect of the compound was also investigated in one p53 mutated breast cancer cell line and in one cervical cancer cell line with disrupted p53 pathway. The cell death percentages are represented in Table 2 below:

TABLE 2

| Cell lines with functional p53 (Death Percentages given) | | | | Cell lines with disrupted p53 (Death Percentages given) | |
|---|---|---|---|---|---|
| A 549: Lung Cancer cell with wild type p53 | HepG2: Liver Cancer cell with wild type p53 | MCF-7: Breast Cancer cell with p53 wild type | Dose | MDA MB 231: Breast Cancer cell with p53 mutation | HeLA: Cervical Cancer Cell with unstable P53 |
| 0% | 0% | 0% | 0.0 Vehicle Control (0.51 mM HCl) | 0% | 0% |
| 1.5 ± 0.29 | 2.75 ± 0.71% | 3.75 ± 0.22% | | 2.5 ± 0.38% | 2.25 ± 0.26% |
| 26 ± 4.32% | 20.75 ± 5.25% | 23.00 ± 7.26% | 15 µM | 36.50 ± 5.00% | 20.5 ± 4.20% |
| 34.25 ± 4.35 | 38.5 ± 6.25%, | 32.5 ± 2.89% | 20 µM | 47.00 ± 6.78% | 37.75 ± 5.44% |
| 47.75 ± 6.34 | 55.86 ± 7.12% | 41.5 + 2.65% | 25 µM | 60.25 ± 9.03% | 46.75 ± 5.38% |

From the above table (Table2) it is clear that the compound showed a dose-dependent increase in cytotoxicity in all the 5 cancer cell lines tested. Interestingly, the highest mortality in each of the three concentrations was observed in the p53 mutated breast cancer cell line with the highest dose exhibiting 60% cell death. However, the cytotoxicity in the cervical cancer cell line having disrupted p53 function was comparable to that of the p53 wild type cell lines. From this cytotoxicity data on a series of cancer cell lines, it can be hypothesized that unlike many chemotherapeutic drugs, this compound can exert its cytotoxic effect on cancer cells irrespective of the cell's p53 status. Another point of interest in the above cytotoxicity data is that between the two breast cancer cell lines, mortality was found to be greater in the p53 mutated cells than the one with wild-type p53.

(C) Cell Cycle Analysis of M2 Treated p53 Mutated Breast Cancer Cell Line.

Cell cycle analyses were performed with the p53 mutated breast cancer cell line to explore deeper into the probable mechanism. Cancer cell line MDA MB 231 (p53 mutated) was maintained in ATCC recommended culture media supplemented with 10% FBS, 100 µg/ml streptomycin and 50 units/ml penicillin, at 37° C. in a humidified incubator containing 5% $CO_2$. For experiments, cells ($10^6$) were plated with 2% serum and then the required experiments were performed. Cells were harvested after 12 hour exposure with the compound at varying concentrations and cell cycle phase distribution of nuclear DNA was determined by flowcytometry using propidium iodide (PI) as DNA-binding fluorochrome.

Results (vide table below) show a dose dependent increase in the sub-GO peak with the treatment doses indicating cell death. Thus, it is clear that the compound was able to induce apoptosis even in the absence of p53. However, the percentage of cells in the S-G2-M phase, which is the proliferative phase, was found to be lowest in the 15 µM dose (Table 3). Analyses of the cells in sub GO phase and S/G2/M are given as mean±Standard Deviation of five independent experiments.

TABLE 3

| Dose | MDA MB 231: Cancer cell with p53 mutation (% Sub $G_0$ as from cell cycle analysis) | MDA MB 231: Cancer cell with p53 mutation (% S/G2/M as from cell cycle analysis) |
| --- | --- | --- |
| 0.0 | 3.08 ± 2.19% | 20.12 ± 1.24% |
| Vehicle Control (0.51 mM HCl) | 2.43 ± 1.16% | 18.78 ± 1.28% |
| 25 µM | 30.50 ± 4.96% | 16.94 ± 4.82% |
| 20 µM | 27.38 ± 2.28% | 12.09 ± 1.77% |
| 15 µM | 16.08 ± 2.28% | 10.76 ± 1.38% |

(D) Cytotoxicity Study of M2 Against Sarcoma180 Cells.

Before entering into the in vivo experiments with solid transplantable tumour model of sarcoma 180, the drug's efficacy was tested against the same tumor cell in vitro. The data is listed in table 4.

TABLE 4

| Dose | Sarcoma 180 (in vitro) (Death Percentages given) |
| --- | --- |
| 0.0 | 0% |
| Vehicle Control (0.51 mM HCl) | 3.00 ± 1.00% |

TABLE 4-continued

| Dose | Sarcoma 180 (in vitro) (Death Percentages given) |
| --- | --- |
| 25 µM | 57.33 ± 4.16% |
| 20 µM | 50.33 ± 5.03% |
| 15 µM | 36.67 ± 6.12% |

From the above in vitro study it is evident that M2 in its soluble form shows anticancer property within the range 15 µM-25 µM without being cytotoxic to normal cells. 30 µM was found to exert cytotoxic effect on human PBMC. Thus for study the effect in vivo, the range was selected from 15 µM to 40 µM. The lower end was selected 15 µM since below that level the anticancer activity was not very significant whereas the upper end was selected 40 µM to check its anticancer activity along with cytotoxic activity towards normal cells.

For In Vivo Anticancer Activity Parameters to be Studied and Techniques to be Used are Noted Hereunder:

Cell Viability Assay

The cytotoxicity of the water soluble M2 at different doses was tested on the proliferation of tumor cells by the Trypan Blue exclusion method. Cells were harvested from the sarcoma tissue and a single cell suspension was made. Those cells that could exclude the Trypan blue dye were counted in haemocytometer as viable cells.

Measurement of Tumor Weight and Volume

The antitumor activity was assessed by measuring the change in tumor volume and tumor weight. Changes in tumor size over time after tumor transplantation was assessed in all the experimental groups. The length and width of the tumor were measured using digital calipers. Tumor volume was calculated by the following formula:

Tumor volume (mm3): 0.5×a×b2 where a is the largest diameter and b its perpendicular.

Dissection and Tissue Collection

All the mice were euthanized after the last dose of M2 treatment on the 21st day. Liver and tumor tissues of the animals from all the experimental groups were collected, washed in 0.9% saline, soaked in filter paper and processed for cellular, biochemical, histological and immunohistochemical studies. Femurs were also aseptically removed; bone marrow was flushed with a 26 gauge needle and suspended in RPMI for cell count and cell cycle analysis.

Tumor and Bone Marrow Cell Count

Cells from tumor tissue were harvested and a single cell suspension was prepared in RPMI supplemented with EDTA and collagenase. A single cell suspension of the bone marrow was made with repeated aspiration. The cells were resuspended in RPMI-1640. The viable tumor and bone marrow cells were counted in a haemocytometer by the Trypan Blue exclusion method.

Tumor and Bone Marrow Cell Cycle Distribution Analysis

For the determination of cell cycle phase distribution of nuclear DNA, cells from bone marrow and tumor tissue ($1×10^6$ cells) were harvested from tumor bearing untreated and treated mice. After making a single cell suspension, cells were fixed with 3% p-formaldehyde, permeabilized with 0.5% Triton X-100, and nuclear DNA was labelled with propidium iodide (PI, 125 µg/ml) after RNase treatment using Cycle TEST PLUS DNA reagent kit. Cell cycle phase distribution of nuclear DNA was determined on FACS Calibur using Cell Quest Software (Becton-Dickinson Histogram display of DNA content (x-axis, PI fluorescence) versus counts (y-axis) has been displayed. Cell Quest statistics was employed to quantitate the data at different phases of the cell cycle.

Detection of Apoptosis

Single Cell Gel Electrophoresis (Comet assay) was performed in sarcoma cells to study the induction of apoptosis by M2. Comet assay is a sensitive, reliable, and rapid method for DNA damage evaluation. The segmented DNA emigrates from the nucleus towards the anode under an electrical current to produce comets. About 400 μl of the cell suspension was mixed with 800 μl 1% low melting point agarose. Then 100 μl of the mixture was layered on slides precoated with a 1% normal melting point agarose and then covered with a cover slip. The slides were then placed in a refrigerator for 5 min. Then cover slips were carefully removed and the slides were left in a dark place except for the positive control slides. The positive control slides were treated with 200 μM $H_2O_2$ solution for 17 min at 4° C., while the negative control slides remained untreated. Then all the slides were immersed in cold lysis solution (2.5 M NaCl, 100 mM EDTA, 0.2 M NaOH, 10 mM Tris, 1% Triton X-100, pH=10), protected from light and refrigerated at 4° C. for 45 min. Slides were then left in freshly prepared electrophoresis solution (0.3 M NaOH, 1 mM EDTA, pH>13,) for 40 min. Electrophoresis was performed using the same solution at 300 mA, 25 V for 45 min. After electrophoresis the slides were neutralized gently with 0.4 M Tris buffer at pH 7.5 for 10 min and stained with 20 μg/ml ethidium bromide for 7 min. Slides were washed and then dried. Two slides were used for each sample and photos were taken from at least 100 cells (50 cells for each slide) using a fluorescent microscope at 400 magnifications. Cells without DNA damage retained a circular appearance. During electrophoresis, DNA with strand breaks migrated toward the anode, giving the cell a "comet" appearance. Comets were counted in four to five different fields of a section, and data are summarized in terms of percent comet. Every experiment was repeated thrice.

Measurement of Serum Biochemical Parameters

Alanine aminotransferase (ALT), aspartate aminotransferase (AST), alkaline phosphatase (ALP) and creatinine levels were measured from collected sera using kits (Sigma).

Measurement of Oxidative Stress Biomarkers

Preparation of Liver and Tumor Tissue 400 mg of liver and tumor liver tissue were homogenized in 1.15% KCl. The homogenate was then centrifuged at 10,000 g at 4° C. for 20 mins. The clear supernatant collected was used for quantitative estimation of lipid peroxidation (LPO), superoxide dismutase (SOD), catalase (CAT), Glutathione-S-Transferase (GST) and protein (Lowry et al., *J. Biol. Chem*, 193, 265-275, 1951).

Assay of LPO (Please Provide Full Form)

The extent of LPO in the bone marrow and liver homogenates was determined quantitatively by performing the method as described by Ohkawa et al (*Anal. Biochem*, 95, 351-358, 1979). The amount of malondialdehyde was measured by reaction with thiobarbituric acid at 532 nm using spectrophotometer. MDA levels were calculated using the standard curve of malondialdehyde and its level expressed in nM/mg of protein.

Assay of Anti-Oxidant Enzymes

CAT (Please Provide Full Form) Activity

CAT activity was assessed by the method of Luck (*Methods of Enzymatic Analysis*, Academic Press, New York, pp. 895-897, 1963), wherein the breakdown of $H_2O_2$ is measured. Briefly, assay mixture consists of 3 mL of $H_2O_2$ phosphate buffer and 0.05 mL of the supernatant of the tissue homogenate. The change in absorbance was recorded for 2 min at 30 s interval at 240 nm using spectrophotometer.

Super-Oxide Dismutase (SOD) Activity

SOD activity was assayed by the method of Marklund et al (Eur. J. Biochem, 47, 469-474, 1974) based on pyrogallol auto oxidation inhibition and expressed as unit/mg of protein. One unit of enzyme activity is defined as the amount of enzyme necessary for inhibiting the reaction by 50%. Auto oxidation of Pyrogallol in Tris-HCL buffer (50 mM, pH 7.5) is measured by increase in absorbance at 420 nm.

Glutathione S-Transferase (GST) Activity

GST activities were measured in tissue cytosol by determining the increase in absorbance at 340 nm with 1-chloro-2,4-dinitrobenzene (CDNB) as the substrate and the specific activity of the enzyme was expressed as formation of CDNB-GSH conjugate per minute per milligram protein (*J. Biol. Chem.* 249, 7130-7139, 1974).

Western Blot Analysis

Cell lysates were obtained and equal amounts of protein from each sample were diluted with loading buffer, denatured, and separated by 10% sodium dodecyl sulfate-polyacrylamide gel electrophoresis (SDS-PAGE) followed by protein transfer to polyvinylidene fluoride membranes (PVDF). The effect of M2 treatment on the expression of certain cell cycle proteins such as p53, p21 and PCNA, ERK3 and on Nrf-2, the regulator of cellular anti-oxidant response was determined. Proteins were detected by incubation with corresponding primary antibodies (anti p53, anti-p21, anti-Nrf-2, anti-ERK3 and anti-PCNA) antibodies followed by blotting with AP-conjugated secondary antibody. The blots were then exposed to NBT/BCIP substrate for detection. This analysis was performed three times.

Statistical Analysis

The experiments were repeated three times and the data were analyzed statically. Values have been shown as standard error of mean, except where otherwise indicated. Data were analyzed and, when appropriate, significance of the differences between mean values was determined by Student's t test. Results were considered significant at $p<0.05$.

Example III: In Vivo Study

After confirming its anti-cancer effect in vitro, the in vivo effect of M2 was further tested in a murine transplantable solid tumor model, Sarcoma-180.

Animals: Male Swiss albino mice, (obtained from animal colony of our Institution) strains will be maintained in plastic cages (~4 mice/cage) at an ambient temperature of 22-25° C. on a 12 hour light/dark cycle with access to drinking water and standard pellet diet ad libitum. Use of animals will be under strict animal care ethics guidelines of the institute.

Dose selection: The doses for in vivo study were determined on the basis of in vitro results taking into account the blood volume of Swiss albino mice to be 2 ml (Riches et al., *J. Phygiol.* 228, 279-284, 1973). The concentrations that were selected are 15 μM (0.4974 mg/kg), 25 μM (0.829 mg/kg), 30 μM (0.9948 mg/kg), 35 μM (1.1606 mg/kg) and 40 μM (1.3264 mg/kg). The total amount of drug which were administered intraperitoneally during this treatment period are: 99.48 μg, 165.8 μg, 198.96 μg, 232.12 μg and 265.28 μg.

In Vivo Tumor Models

Model A: Sarcoma 180 Transplantable Tumor

The murine Sarcoma-180 (S-180) cells used in this study were maintained in vivo by weekly intraperitoneal passage of 1×10⁶ cells in male Swiss albino mice. Solid tumors were produced by subcutaneous inoculation of 1×10⁶/ml S-180 cells on the dorsal surface of right hind leg of Swiss albino mice. Viability was assessed by the Trypan blue dye exclusion method.

Model B: Ehrlich's Ascites Carcinoma

Ehrlich's ascites carcinoma (EAC) cells were maintained by serial intra-peritoneal passage of $10^5$ cells per mice. EAC cells were collected from tumor-bearing mice at the exponential phase of growth, roughly 7 days after tumor transplant. The cells were drawn out aseptically with the help of a fine needle. The cells were washed in PBS and counted with the help of a Hemocytometer by the Trypan Blue dye exclusion test. The cells were suspended in PBS and inoculated into the next batch of mice.

Experimental Groups (Model A):
Gr 1 saline treated normal mice
Gr 2 Tumor bearing (S-180) control mice
Gr 3 Tumor bearing (S-180) animals treated with 15 µM M2
Gr 4 Tumor bearing (S-180) animals treated with 25 µM M2
Gr 5 Tumor bearing (S-180) animals treated with 30 µM M2
Gr 6 Tumor bearing (S-180) animals treated with 35 µM M2
Gr 7 Tumor bearing (S-180) animals treated with 40 µM M2

Experimental Groups (Model B):
Gr 1 saline treated normal mice
Gr 2 Tumor bearing (EAC) control mice
Gr 3 Tumor bearing (EAC) animals treated with 35 µM M2

Results Obtained with Sarcoma-180 Tumor Model (Model A)

(A) Anti-Tumorigenic Activity of M2

Figure 1:
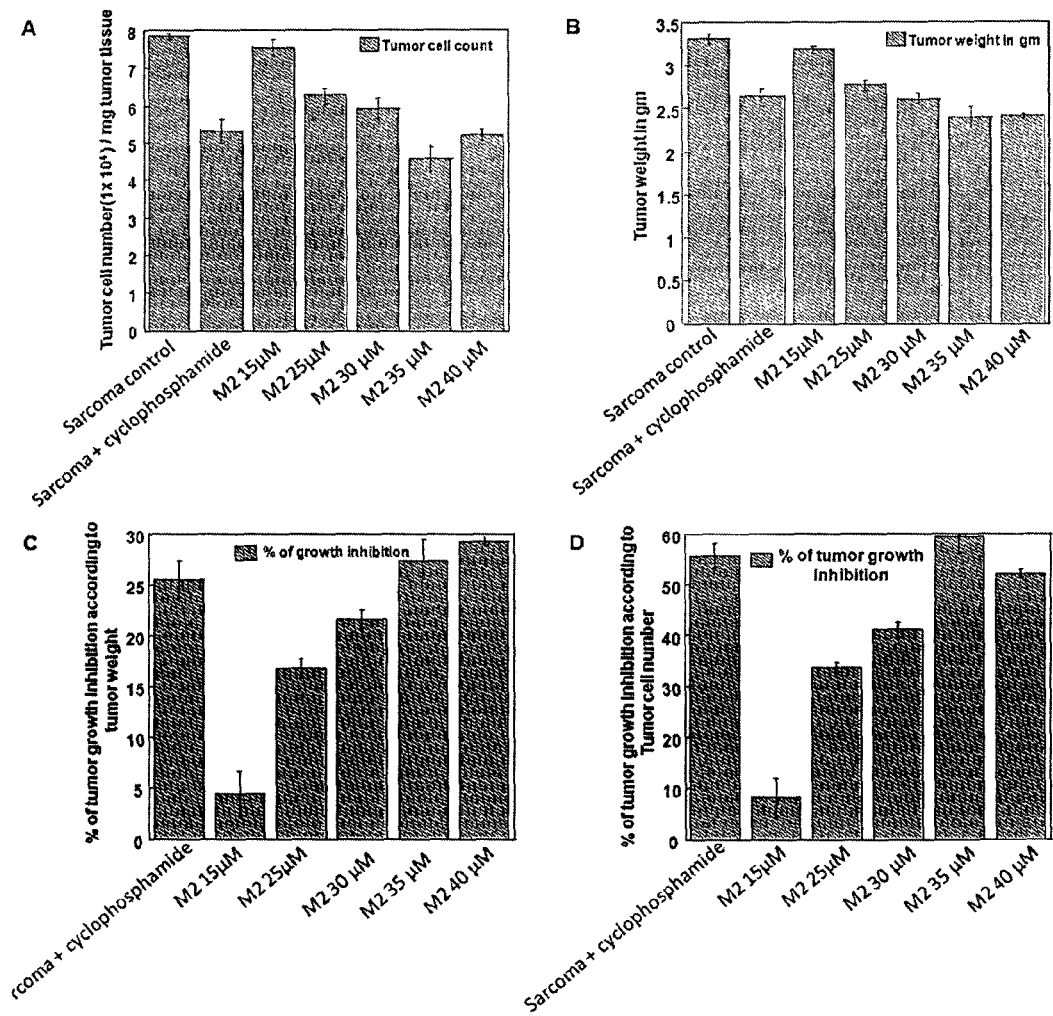
Figure 2:
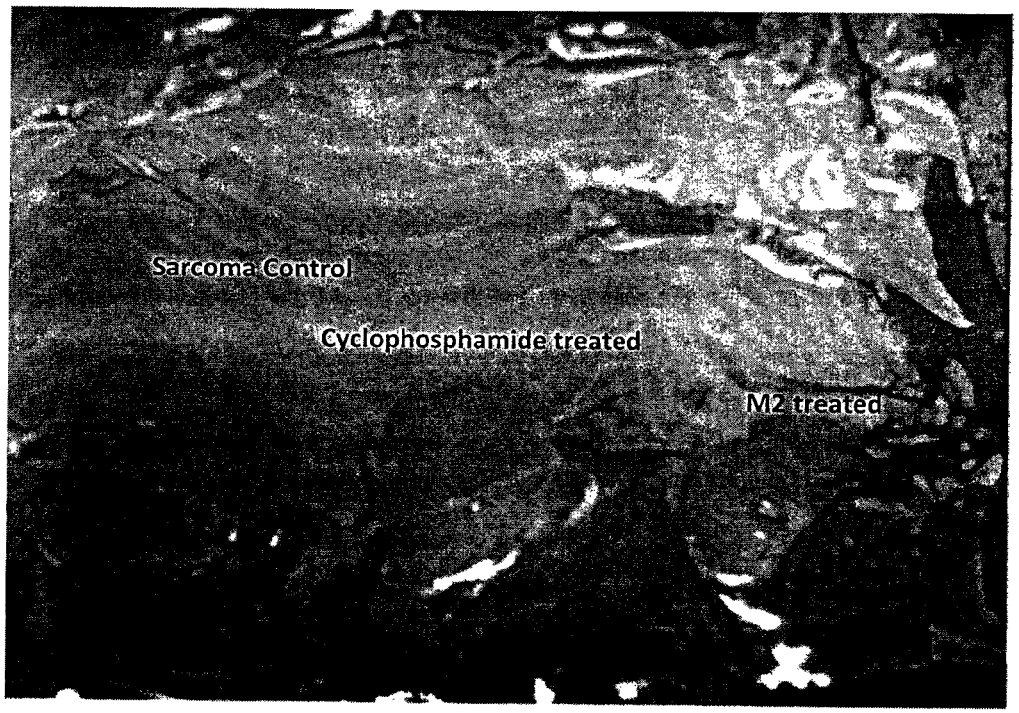

The tumoricidal effects of M2 was compared with that of a conventional chemotherapeutic agent, cyclophosphamide. Tumor cell count, tumor weight (FIGS. 1 A & B) has been compared in different groups of experimental animals. Treatment with all the 5 doses of M2 resulted in a significant decrease in tumor weight and tumor cell count ($p<0.05$) compared to the Sarcoma Control (SC) group, thus exhibiting promising antitumor activity. Tumor weight showed a dose dependent decrease with M2 treatment. A dose dependent decrease in tumor cell count was also observed upto the 35 µM dose. The 40 µM dose showed a slightly lesser inhibition in tumor cell count. The percentage inhibition in tumor weight and tumor cell count is plotted in FIGS. 1 C & D. Interestingly, M2 treatment was significantly more effective than cyclophosphamide treatment (FIG. 2) both in terms of tumor weight and tumor cell count.

(B) Modulation of Cell Cycle Phase Distribution of Tumor Cells by M2

Figure 3:
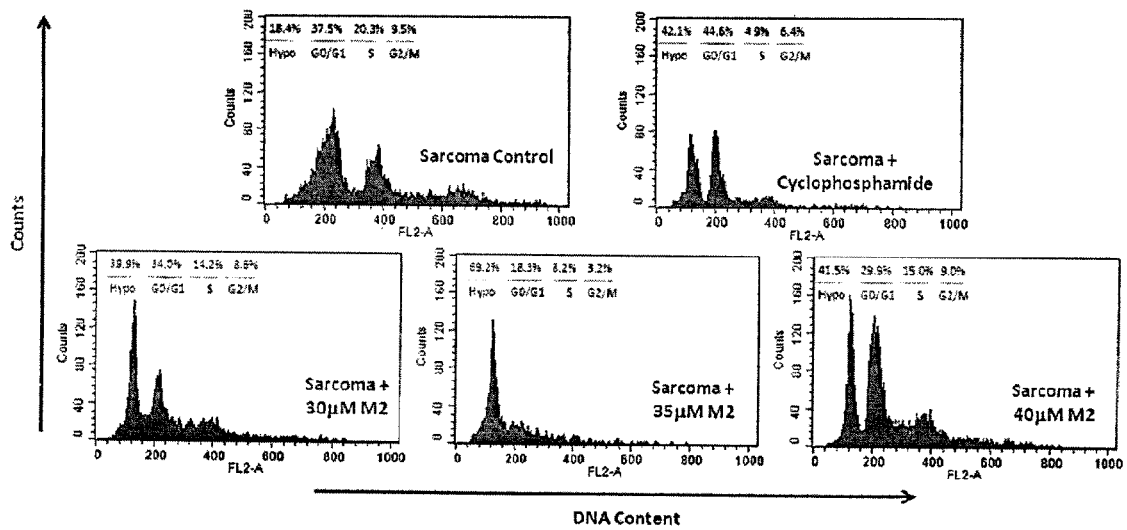

Treatment with M2 resulted in a significant increase in the sub-GO region (hypolpoidy population) at all doses administered; FIG. 3 shows representative data of the various experiments. As compared to 18.4% cells in the hypoploidy region of the SC group and 42.1% in the cyclophosphamide treated group, M2 treatment recorded 39.94%, 69.2% and 41.5% hypoploid cells respectively for 30 µM, 35 µM and 40 µM concentrations. The proliferative stage, as estimated by the sum of S and G2/M, also showed distinctive depression in M2 treated groups as compared to the untreated counterparts.

(C) Effect of M2 on Tumor Cell Apoptosis

Figure 4:
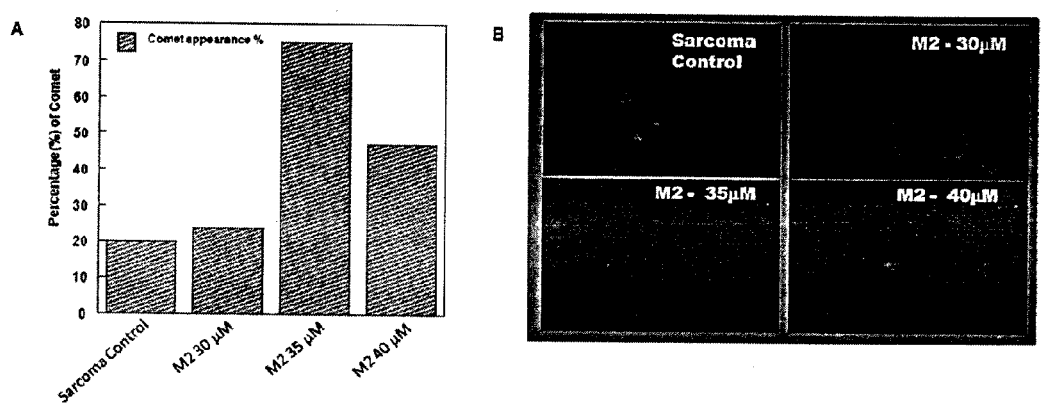

The induction of DNA damage in the tumor cells thereby inducing apoptosis after M2 treatment was investigated by Comet assay. Treatment with M2 caused significant DNA damage in the tumor cells as is evident by the increase in the percentage of 'comet' cells per field of the slides studied (FIG. 4) as compared to the untreated sarcoma control group. Thus, the observed reduction in tumor volume, tumor weight and tumor cell count in the M2 treated groups can be attributed to the induction of apoptosis in tumor cells by M2 treatment.

(D) Effect of M2 on Liver and Kidney Function of Treated Host

Figure 5:
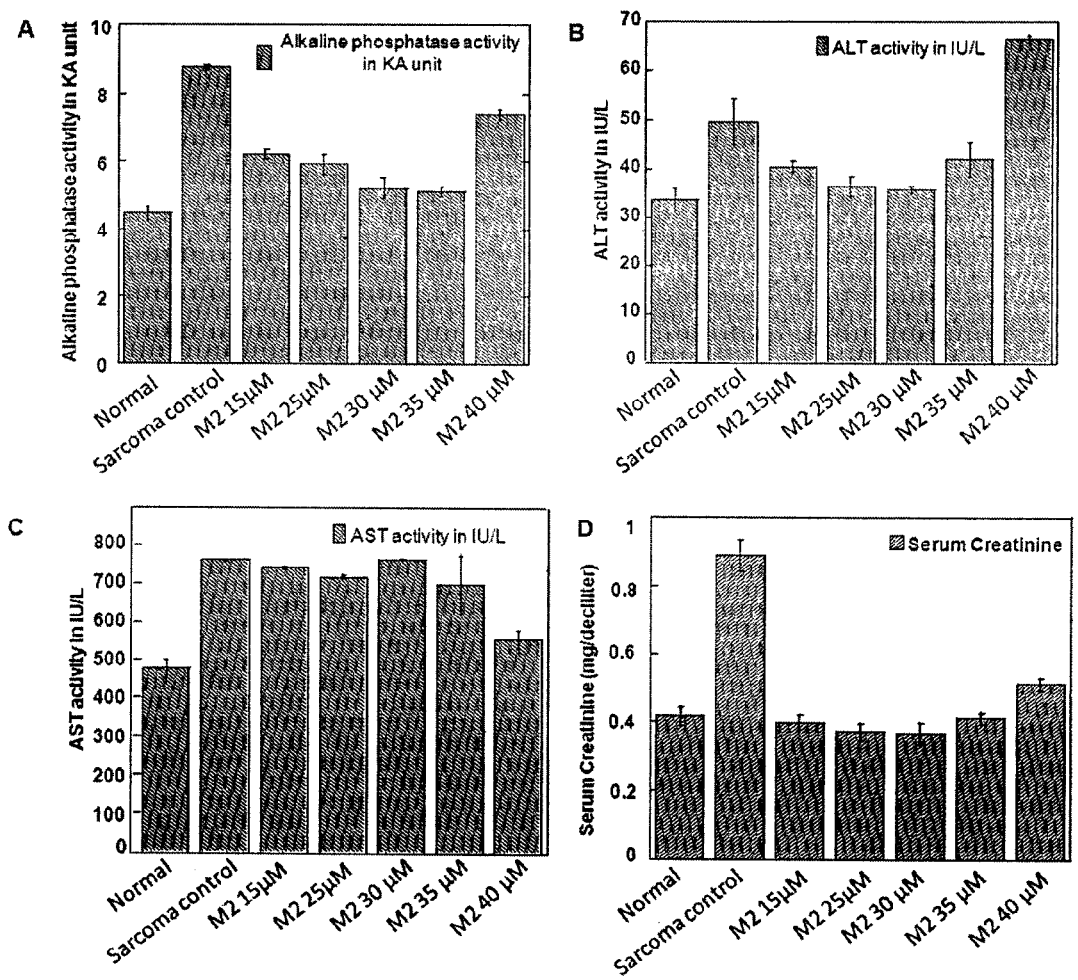
FIG. 5 illustrates effect of M2 on serum biochemical markers of toxicity. A) Alkaline Phosphatase level (AP) B) Alanine aminotransferase (ALT) levels C) aspartate aminotransferase (AST) levels & D) Creatinine levels.

Serum alanine aminotransferase (ALT), aspartate aminotransferase (AST), alkaline phosphatase (ALP) values and creatinine levels of all the M2 treated groups were within the normal range except for the highest dose (FIG. 5). This suggests that M2 drug, except the 40 µM concentration, is non-toxic in all the other doses.

(E) Effect of M2 on Hepatic Oxidative Stress and Anti-Oxidant Enzymes

Figure 6:
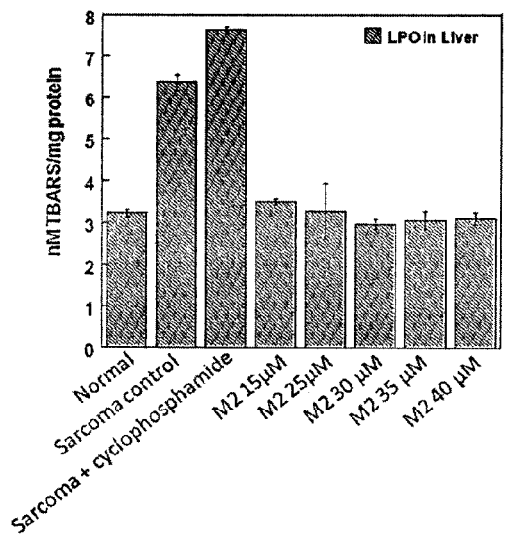
FIG. 6 illustrates Effect of M2 on hepatic oxidative stress. The extent of LPO in the liver homogenates was determined quantitatively by reaction with thiobarbituric acid at 532 nm using spectrophotometer and expressed as nM MDA/mg protein.

The effect of the compound on the redox status of normal tissues was investigated by detecting the LPO levels in the liver of treated and untreated tumor bearers. FIG. 6 shows the modulation of hepatic LPO by different doses of M2 as compared with normal, SC and tumor-bearers treated with cyclophosphamide. Livers of sarcoma control mice showed a rise in LPO levels as compared to that of normal mice. Treatment with cyclophosphamide further enhanced this hepatic oxidative stress. However, the levels of LPO showed a significant decrease ($p<0.05$) in all the M2 treated tumor bearers and was found to be comparable to normal values.

FIG. 7 shows changes in the activity of hepatic anti-oxidant enzymes, viz. SOD, CAT and GST in all the experimental groups of mice. Treatments with M2 lead to an increase in all the enzyme activities as compared to the normal as well as the sarcoma control mice. Particularly effective doses were found to be that of 30 µM and 35 µM concentrations. Moreover, a comparison of the effect of M2 and cyclophosphamide on the anti-oxidant enzymes suggests that the latter causes a depression in the activity of hepatic anti-oxidant enzymes creating oxidative stress in the host.

Thus, M2 does not induce oxidative stress in normal tissues of the host unlike the commonly used chemotherapeutic agent cyclophosphamide.

(F) Effect of M2 on Bone Marrow Cellularity

The conventional chemotherapeutic drug, cyclophosphamide, is known to induce severe myelosuppression in the host. Hence, in order to compare this side-effect of cyclophosphamide with M2, the effect of M2 on this primary immune organ was tested. Quite interestingly, despite having significant anti-tumorigenic activity which is greater than cyclophosphamide, even the highest dose of M2 did not cause bone marrow suppression in the tumor bearers. FIG. 8 depicts the bone marrow cell counts in normal and experimental animals. In the Sarcoma control as well as the Cyclophosphamide treated sarcoma group, there is a significant depression in bone marrow cell count ($p<0.05$) which was ameliorated to a significant extent by administration of M2 in the tumor bearing mice ($p<0.05$). The changes in bone marrow cell cycle phase distribution in normal and experimental groups are depicted in FIG. 9. The severe myelosuppression following Cyclophosphamide treatment can be attributed to the increase in the hypoploidy peak viz. 48.5% as compared to only 5.5% in the normal and 20.9% in the sarcoma control group. Furthermore, a decrease in the proliferative phases (S and G2/M combined) viz. 3% in CP as compared to 21.23% in the normal and 15.15% in the sarcoma control groups. Treatment with M2, however, reduced the hypoploidy peak significantly (5.4% only in the 40 µM concentration) as compared with sarcoma control or tumor bearers treated with cyclophosphamide. Furthermore unlike the cyclophosphamide treated groups, M2 treatment did not decrease the proliferative phase as compared to sarcoma control groups.

G) Effect of M2 on the Nrf-2 Protein Levels in Liver

In order to further validate the anti-oxidative effect of M2 on the host hepatic system, the expression of Nrf-2 protein was studied by Western Blotting. Nrf-2 is an important transcription factor that regulates the antioxidant response by inducing the expression of anti-oxidant enzymes. M2 was found to modulate the expression of hepatic Nrf-2 in a manner which complements observed biochemical findings (FIG. 10A). In the liver, Nrf-2 expression increased with M2 treatment when compared to the sarcoma control group.

(H) Effect of M2 on Proliferation Marker PCNA in Bone Marrow

In order to further establish the non-toxicity of M2 in the bone marrow compartment, the expression of the proliferation marker, PCNA, was studied by Western Blotting. PCNA expression showed a significant increase in all the M2 treated groups as compared to the sarcoma control group (FIG. 10B) which shows that M2 does not cause bone-marrow suppression which is a hallmark side-effect of the conventional chemotherapeutic drug cyclophosphamide.

(I) Effect of M2 on Tumor Tissue PCNA and Kinase

Expression of the proliferation marker, PCNA, as determined in the tumor tissues by Western Blotting, was found to decrease by M2 treatment which supports the anti-proliferative effect of the compound (FIG. 11A).

Kinases have become one of the most intensively pursued classes of drug target. Thus, in order to assess the effect of M2 on kinases, the expression of ERK was detected in tumor tissues of treated and untreated groups by Western Blotting. M2 Was able to significantly reduce the expression of ERK as compared to the sarcoma control as well as the cyclophosphamide treated groups (FIG. 11B).

Results Obtained with EAC Tumor Model (Model B)

Antitumorigenic Activity of M2 in EAC

Treatment with the most effective dose of M2 (35 µM) resulted in a significant reduction in both tumor volume and tumor cell count in the EAC bearing mice as compared to EAC control and cyclophosphamide treated EAC tumor bearing mice (FIGS. 12 A, B & C). This confirms the potent antitumorigenic activity of M2 in yet another in vivo tumor model.

Effect of M2 on Bone Marrow Cellularity

As in S-180 tumor bearing mice discussed above, M2 was found to have a protective effect on bone marrow in EAC tumor bearing mice unlike cyclophosphamide which induces myelosuppression in EAC tumor bearing mice (FIG. 13). Thus, the significant antitumor effect of M2 was not accompanied with any undesirable toxicity to bone marrow in EAC tumor bearing mice unlike cyclophoshamide which induces myelosuppression.

In this respect it is again a selective finding of the present invention that surprisingly compound Bis[(3-[4-({[3-({4-[(2cyanoethyl)(methyl)amino]benzylidene}amino)propyl]imino}methyl)(methyl)anilino]propanenitrile)] (M2) was specifically identified after such extensive studies to be found to bind intramolecular G-Quadruplex DNA structure and other potential quadruplex forming sequences over duplex DNA structures potentially effective as cancer therapeutic for said cancer therapeutic activity in effective amounts of 15 µM-40 µM/0.4974 mg/kg-1.3264 mg/kg for intervening with different signaling pathways and/or for down regulating the functions of different proteins associated in cancer biology thereby adapted as effective kinase suppressing and/or any other signaling pathway interfering agent and/or formulations involving the same.

The selection of a target such as the G-Quadruplex DNA structure is an essential step to design a potent binder or stabilizer for the G-Quadruplex, which exists as repeats at the 3' telomeric region of chromosome, promoter region of oncogenes and some promoter regions of kinase genes. It is the selective finding of the present advancement that only when the structure so selected has a preferred disposition in crowded organic medium only then can it be actually correlated with the natural structures preferred in the nuclear matrix. Such an effective G-Quadruplex (2LD8.pdb) structure could be only selectively attained by way of extensive studies and analysis under the present advancement from a crowded medium, wherein the G-face of the Quadruplex is selectively exposed for binding with a ligand. Importantly since the same composition of said Quadruplex exists as different structural form in aqueous solution, it was a challenge to reach to such structure by the techniques available to enable probing the G-face-ligand interaction with various molecules and reach to the drug molecules adapted as new chemical therapeautics of cancer, which is thus solved and selectively attained by way of the present advancement and considered to be very special and technically targeting the intended objectives of the present advancement.

Two types of binding sites were found oven the selective G-Quadruplex (2LD8.pdb) structure from SiteMap analysis (FIG. 14). From the structural view these two binding sites are classified as (a) loop region, having shape of small cavities; (b) co-facial/end stacking region present the top of macromolecule. The loop regions are highly rich in electron density and are favorable for binding with small molecular fragments. These loop regions provide good binding affinity to hydrogen bond acceptors.

To the other binding site i.e. the co-facial end stacking region containing the stacked guanine residues (G-face) (forming first quartet) is enriched with π-electron clouds from all four directions. This site is thus important to develop the advanced G-Quadruplex stabilizing agents/formulations involving the same as it is the most suitable region for small molecules, peptides or DNA, RNA aptamers that fetches favorable entropy to the system resulting in its stabilization.

FIG. 15 depicted the Interactions between different parts of M2 and the G-Quadruplex. In cancer pathology, above said water soluble cancer chemotherapeutic/kinase suppressors and/or any other multisignalling pathway interfering agent/formulations comprising M2 may also bind to the promoter regions of several oncogenes where G quadruplex structures form. Theoretically it is found that M2 can bind to the C-Myc quadruplex (FIG. 16).

Example IV: Spectroscopic Studies of G-Quadruplex Stabilizing Agents

Fluorescence studies: Fluorescence emission pectroscopy was used for analyzing the binding behavior of molecule M2 with G-Quadruplex 5'-TAGGG(TTAGGG)$_3$-3'. A G-rich DNA duplex is used as a control in this study with sequence:

```
5' - GCGCATGCTACGCG - 3'

3' - CGCGTACGATGCGC - 5'
```

The emission spectra of a DNA duplex and G-Quadruplex sequence were recorded at room temperature using Hitachi spectrometer (F-700 FL spectrophotometer) with one cm path-length quartz cuvette. The emission spectrum was recorded from 300-500 nm with an excitation wavelength of 260 nm. Excitation and emission slits were set to 5 nm each.

Emission spectra were recorded by titrating small molecules up to 50 μM concentration against 10 μM G-Quadruplex and duplex DNA.

A significant hypsochromic shift or blue shift n fluorescence emission provides strong evidence whether a drug/ligand molecule binds to G-Quadruplex or not. The fluorescence experiment was carried out by titrating the molecule M2 (0-50 μM) with G-Quadruplex, 5'-TAGGG(TTAGGG)$_3$ (10 μM). The characteristic emission of the spectrum was shown in FIG. 5. A total of 18 nm hypsochromic shifts in G-Quadruplex emission spectra was observed when M2 binds to it (FIG. 17A). The change in fluorescence emission maxima of G-Quadruplex as a function of concentration of ligand molecule M2, yields an equilibrium dissociation constant ($K_D$) of 31±1.2 μM (FIG. 17B). A control experiment was performed for a GC rich DNA duplex,

```
5' - GCGCATGCTACGCG - 3'
3' - CGCGTACGATGCGC - 5'
``` in presence of M2. Interestingly it has been observed that no blue shift on the emission spectra of DNA duplex happened upon the addition of ligands (FIG. 17C). This experimental evidence showed that M2 is highly selective binder to G-Quadruplex structures over the DNA duplex.

The examples discussed hereinbefore are the best embodiments for the present invention and do not limit the scope of the invention.

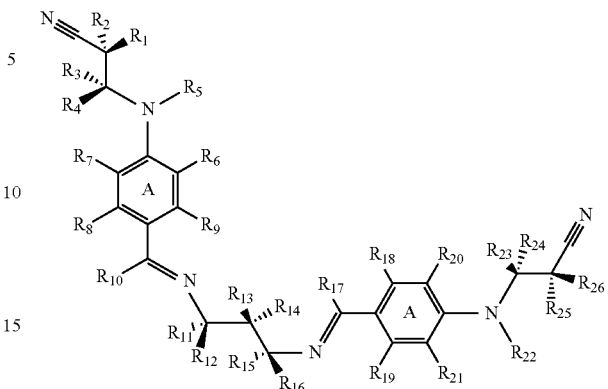

(I)

or pharmaceutically acceptable salts thereof
wherein, $R_1/R_2/R_3/R_4/R_{11}/R_{12}/R_{13}/R_{14}/R_{15}/R_{16}/R_{23}/R_{24}/R_{25}/R_{26}$ are, independently, Hydrogen, Halo, Acyclic/Cyclic hydrocarbon, Homo or HeteroAromatic, Amino, Amide, Ester, Aldehyde, Ketone, Sulfide, Alkyl halide, Aromatic Halide, Enol, Unsaturated alkenes or alkynes with acid-amide, amine, or halo functionalization;
$R_6/R_7/R_8/R_9/R_{18}/R_{19}/R_{20}/R_{21}$ are independently, Hydrogen, Halo, Acyclic/Cyclic hydrocarbon, Homo or hetero aromatic group with or without functionalization

We claim:
1. A cancer chemotherapeutic agent comprising general formula (I)

fused with A (when one group is fused the other group attached to the same side of Aromatic ring does not arise), Amino, Amide, Ester, Aldehyde, Ketone, Sulfide, Alkyl halide, Aromatic Halide, Enol, Unsaturated alkenes or alkynes with acid-amide, amine, or halo functionalization;

$R_5/R_{22}$ are, independently, Methyl, Hydrogen, Halo, Acyclic/Cyclic hydrocarbon, Homo or hetero aromatic group with or without functionalization, Amino, Amide, Ester, Aldehyde, Ketone, Sulfide, Alkyl halide, Aromatic Halide, Enol, Unsaturated alkenes or alkynes with acid-amide, amine, or halo functionalization;

$R_{10}/R_{17}$ are, independently, Hydrogen, Halo, Acyclic/Cyclic hydrocarbon, Homo or hetero aromatic group with or without functionalization, Amino, Amide, Ester, Aldehyde, Ketone, Sulfide, Alkyl halide, Aromatic Halide, Enol, Unsaturated alkenes or alkynes with acid-amide, amine, or halo functionalization.

2. The cancer chemotherapeutic agent according to claim 1, wherein the agent is a comprising Bis(3-[4-({[3-({4-[(2 cyanoethyl)(methyl)amino]benzylidene}amino)propyl]imino}methyl)(methyl)anillno]propanenitrile) compound of Formula II

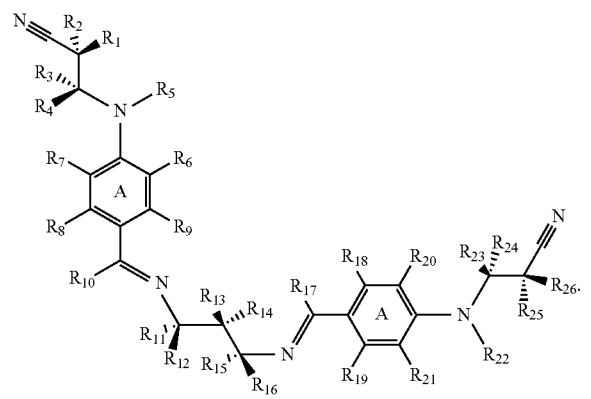

3. The cancer chemotherapeutic agent according to claim 1, wherein the agent is a water soluble form of the molecule of general formula (I) with at least one cationic nitrogen 4. The cancer chemotherapeutic agent according to claim 3, wherein the general formula (I) comprises two protonated nitrogens having the structures as represented hereunder

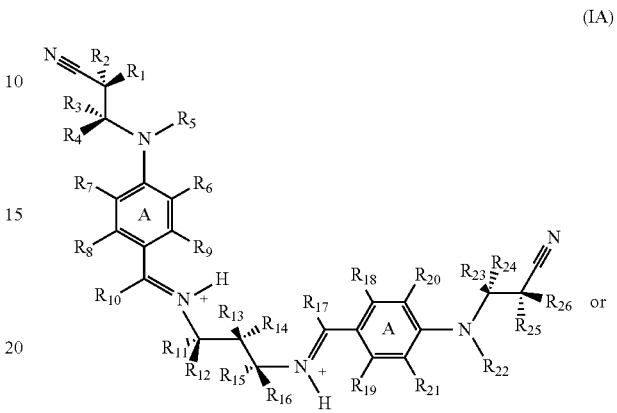

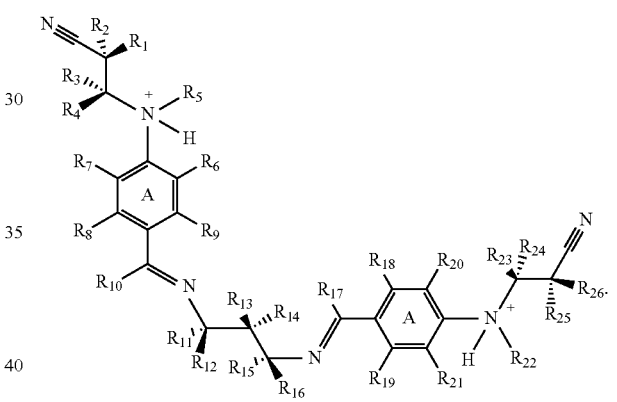

5. The cancer chemotherapeutic agent according to claim 3, wherein the general formula (I) with four protonated nitrogens has the structure as represented hereunder

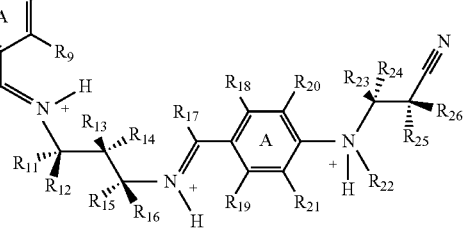

6. The cancer chemotherapeutic agent according to claim 3, having the structure as represented hereunder as formula II

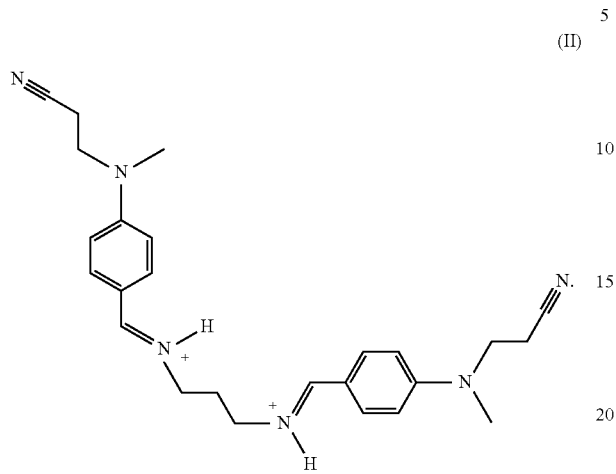
(II)

7. A pharmaceutical formulation/composition comprising the therapeutic agent according to claim 1, and one or more pharmaceutically acceptably carriers or excipients.

8. The pharmaceutical formulation/composition according to claim 7, wherein the formulation/composition is a tablet, suspension, syrup, dispersion, or a form suitable for injection.

* * * * *

UNITED STATES PATENT AND TRADEMARK OFFICE
CERTIFICATE OF CORRECTION

PATENT NO. : 9,682,926 B2
APPLICATION NO. : 14/428836
DATED : June 20, 2017
INVENTOR(S) : Subhrangsu Chatterjee et al.

It is certified that error appears in the above-identified patent and that said Letters Patent is hereby corrected as shown below:

On the Title Page

Column 2, Item (57) under ABSTRACT, Line 5, delete "potential the"

In the Claims

Column 29, Line 67, Claim 1, after "(I)" insert -- : --

Column 30, Lines 1-19, Claim 1, delete "

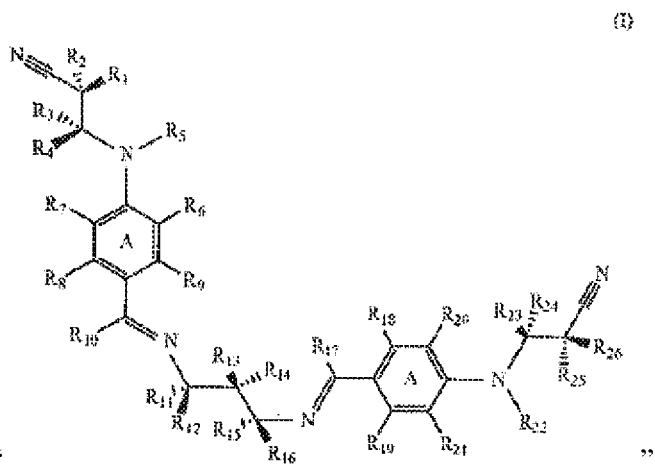

"

Signed and Sealed this
Seventh Day of November, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,682,926 B2

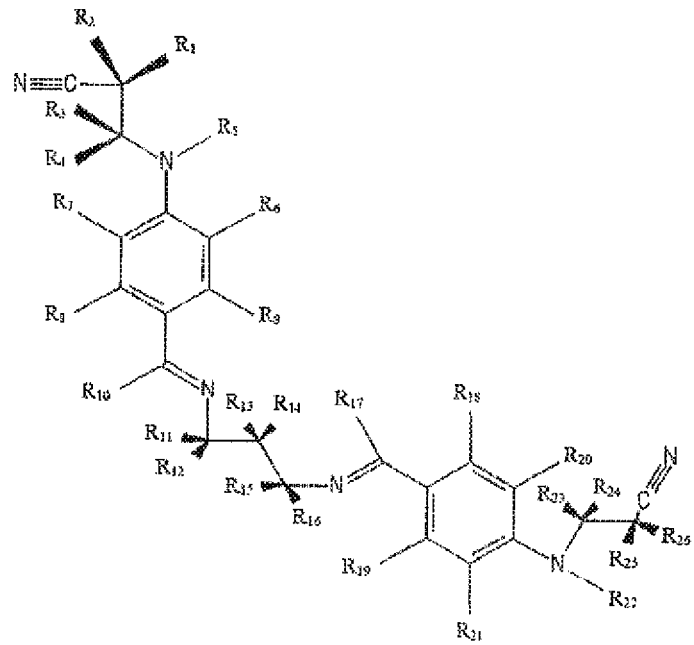

and insert --

Column 30, Line 20, Claim 1, before "or" insert -- , --

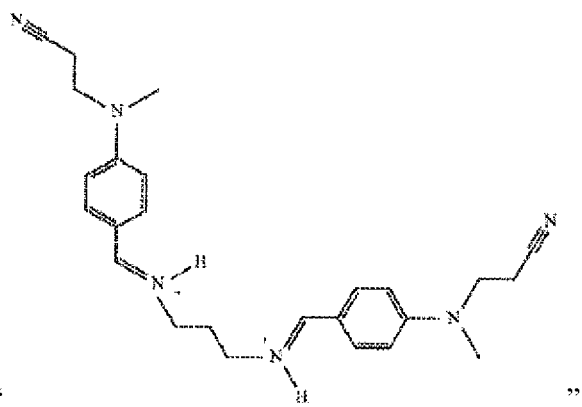

Column 31, Lines 25-43, Claim 2, delete "                                        "

(II)
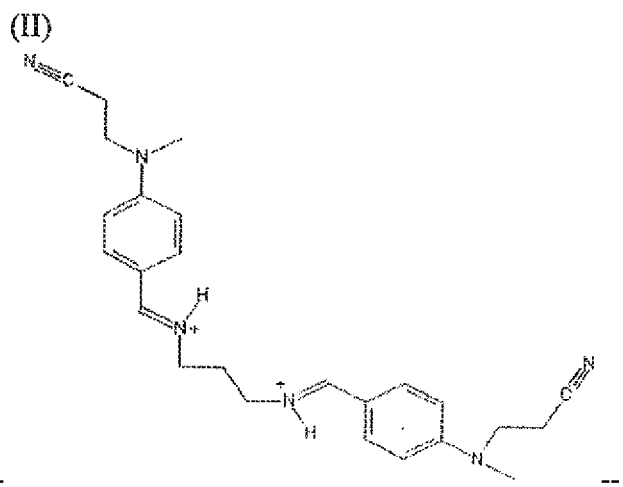
and insert --                                                                 --
Column 31, Lines 49-65, Claim 3, delete
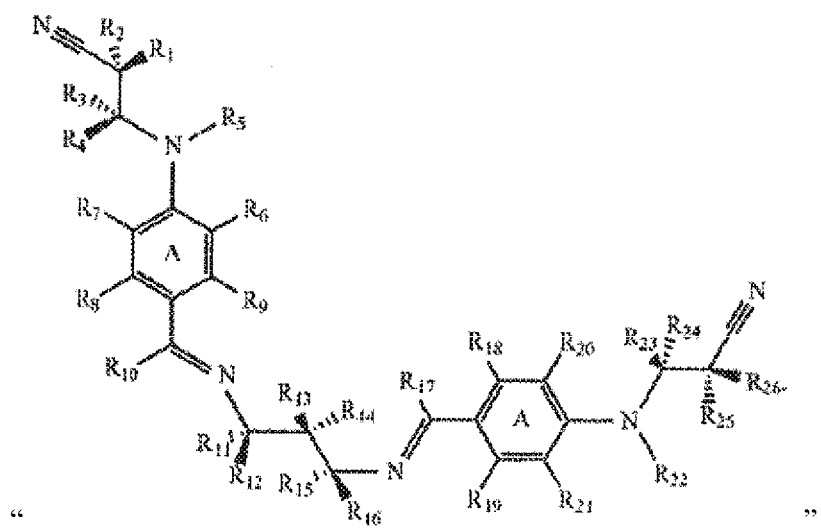
" "

CERTIFICATE OF CORRECTION (continued)
U.S. Pat. No. 9,682,926 B2

(I)

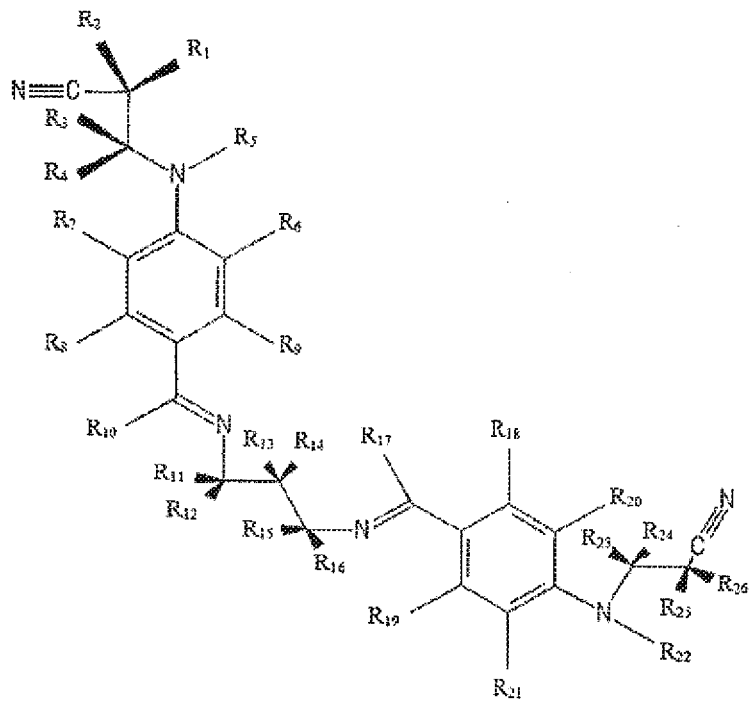

and insert --

Column 32, Lines 6-24, Claim 4, delete (IA)

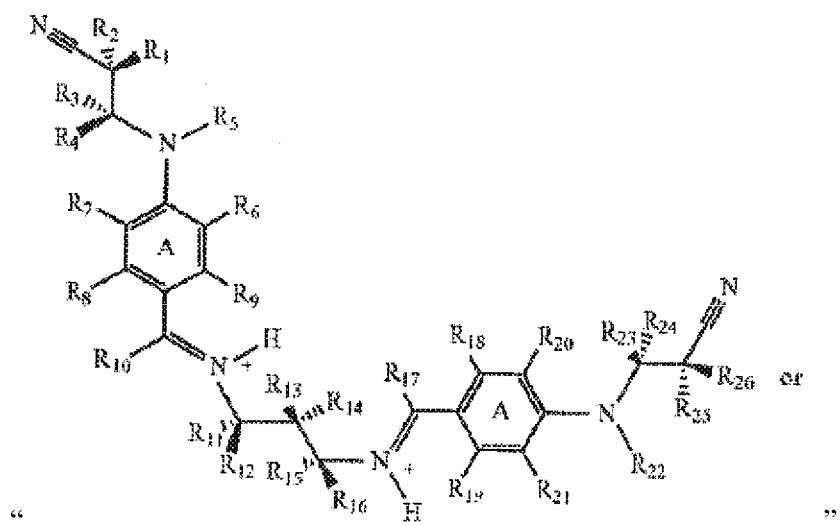

" "

CERTIFICATE OF CORRECTION (continued)
U.S. Pat. No. 9,682,926 B2 and insert --

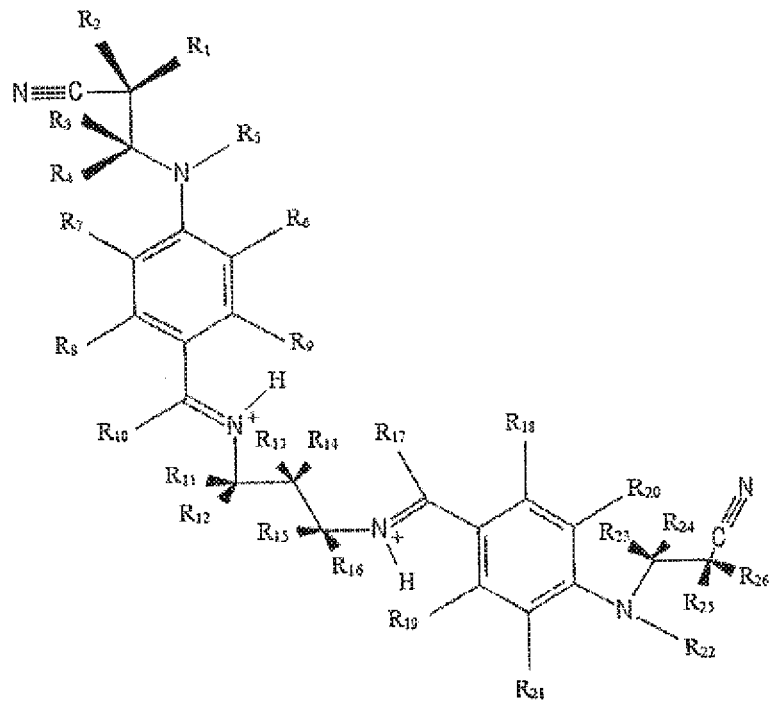

Column 32, Lines 26-42, Claim 4, delete " " " "

(1B)
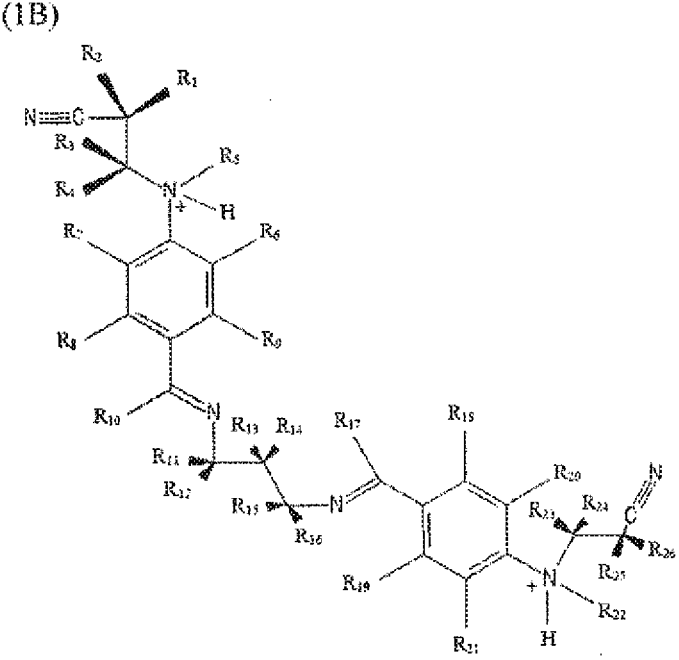
and insert --                                                                                                    --
Column 32, Lines 50-65, Claim 5, delete
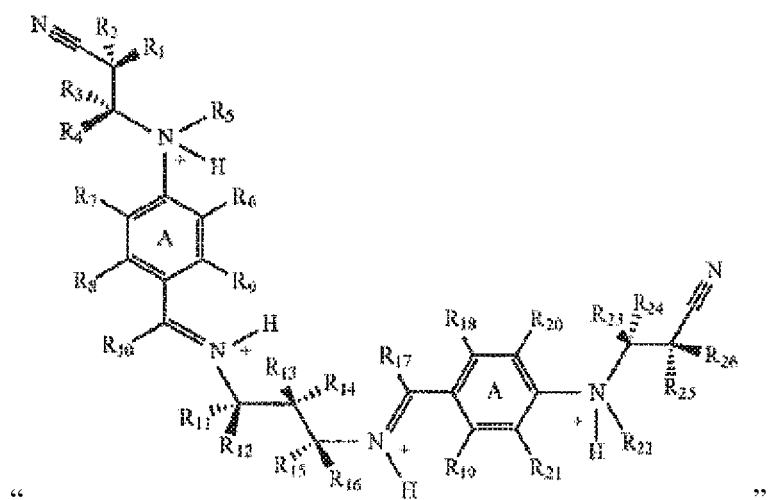
"                                                                                                    "

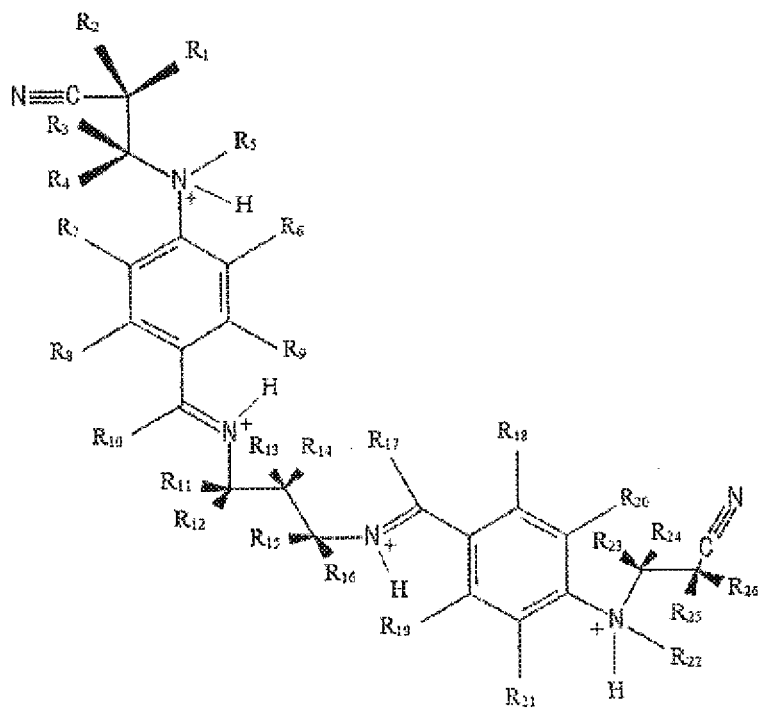
and insert --
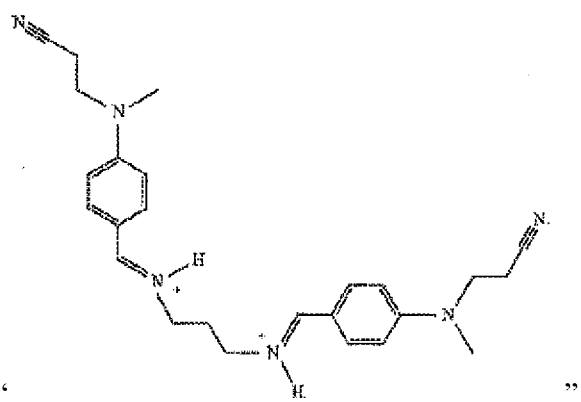
Column 33, Lines 5-23, Claim 6, delete "
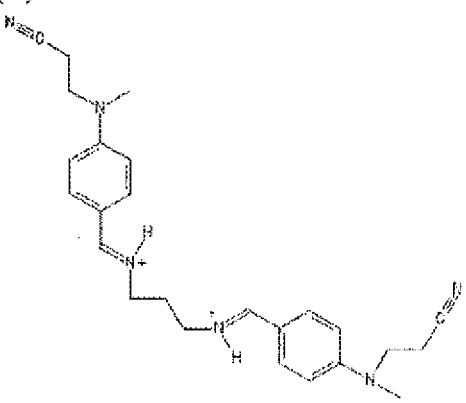
and insert --    --

SEQUENCE LISTING

```
<160> NUMBER OF SEQ ID NOS: 3

<210> SEQ ID NO 1
<211> LENGTH: 14
<212> TYPE: DNA
<213> ORGANISM: Artificial Sequence
<220> FEATURE:
<223> OTHER INFORMATION: G-rich DNA Duplex

<400> SEQUENCE: 1
gcgcatgcta cgcg                                                    14

<210> SEQ ID NO 2
<211> LENGTH: 14
<212> TYPE: DNA
<213> ORGANISM: Artificial Sequence
<220> FEATURE:
<223> OTHER INFORMATION: G-rich DNA Duplex

<400> SEQUENCE: 2
cgcgtacgat gcgc                                                    14

<210> SEQ ID NO 3
<211> LENGTH: 23
<212> TYPE: DNA
<213> ORGANISM: Artificial Sequence
<220> FEATURE:
<223> OTHER INFORMATION: G-Quadruplex

<400> SEQUENCE: 3
tagggttagg gttagggtta ggg                                          23
```